(12) United States Patent
Hiraishi et al.

(10) Patent No.: US 11,155,519 B2
(45) Date of Patent: Oct. 26, 2021

(54) METHOD FOR MANUFACTURING DIASTEREOMER OF CITRIC ACID DERIVATIVE

(71) Applicants: OTSUKA PHARMACEUTICAL FACTORY, INC., Tokushima (JP); ADABIO CO., LTD., Gunma (JP)

(72) Inventors: Katsuya Hiraishi, Gunma (JP); Hiroyuki Soma, Gunma (JP); Fumie Jimma, Gunma (JP); Taro Adachi, Gunma (JP); Ippei Yamaoka, Tokushima (JP); Naoyuki Endo, Tokushima (JP)

(73) Assignees: OTSUKA PHARMACEUTICAL FACTORY, INC., Tokushima (JP); ADABIO CO., LTD., Gunma (JP)

( * ) Notice: Subject to any disclaimer, the term of this patent is extended or adjusted under 35 U.S.C. 154(b) by 42 days.

(21) Appl. No.: 16/606,376

(22) PCT Filed: Apr. 23, 2018

(86) PCT No.: PCT/JP2018/016495
§ 371 (c)(1),
(2) Date: Oct. 18, 2019

(87) PCT Pub. No.: WO2018/199040
PCT Pub. Date: Nov. 1, 2018

(65) Prior Publication Data
US 2020/0055821 A1 Feb. 20, 2020

(30) Foreign Application Priority Data
Apr. 28, 2017 (JP) .............................. JP2017-089725

(51) Int. Cl.
*C07D 207/416* (2006.01)
*A61P 1/16* (2006.01)

(52) U.S. Cl.
CPC ............ *C07D 207/416* (2013.01); *A61P 1/16* (2018.01); *C07B 2200/13* (2013.01)

(58) Field of Classification Search
CPC ................................................ C07D 207/416
See application file for complete search history.

(56) References Cited

U.S. PATENT DOCUMENTS

2016/0237213 A1  8/2016  Lansbergen et al.
2018/0334452 A1  11/2018  Lansbergen et al.

FOREIGN PATENT DOCUMENTS

| JP | 4842624 | 12/2011 |
| JP | 5577129 | 8/2014 |
| TW | 201720791 | 6/2017 |
| WO | 2015/052342 | 4/2015 |
| WO | 2016/164437 | 10/2016 |
| WO | 2017/077707 | 5/2017 |

OTHER PUBLICATIONS

"J. Agric, FoodChem., 47", 1999, pp. 828-831.
"Jounal of Hemorheology Research 1", 1998, pp. 65-67, final page contains English abstract.
"Journal of Hemorheology Research 3", 2000, pp. 81-88, final page contains English abstract.
Chenevert et al., "Regio- and enatioselecti vi ty of the enzyme-catalyzed hydros is of citric acid derivatives", Tetrahedron: Asmmetry, vol. 9, No. 24, 1998, pp. 4325-4329.
Drechsel et al., "Stereochemical characterization of rhizoferrin and identification of its dehydration products", BioMetals, vol. 5, No. 3, 1992, pp. 141-148.
Konetschny et al., "Staphyloferrin A: a structurally new siderophore from staphylococci", European Journal of Biochemistry, vol. 191, No. 1, 1990, pp. 65-74.
Koning et al., "Novel renewable alkyd resins based on imide structures", Journal of Coating Technology and Research, vol. 14, No. 4, 2017, pp. 783-789.
Schmelz et al., "AcsD catalyzes enantioselecti ve citrate desymmetrization in siderophore biosynthesis", Nature Chemical Biology, vol. 5, No. 3, 2009, pp. 174-182.

(Continued)

*Primary Examiner* — Rebecca L Anderson
(74) *Attorney, Agent, or Firm* — Greenblum & Bernstein, P.L.C.

(57) ABSTRACT

By using ion exchange column chromatography or calcium carbonate to an aqueous solution containing a compound A represented by the following formula and citric acid, citric acid in the aqueous solution is removed and a crystalline compound A is obtained by being thereafter subjected to several steps. Further a high-purity noncrystalline compound A is obtained by using calcium carbonate, sulfuric acid, an organic solvent and the like to the aqueous solution containing the compound A and citric acid to remove citric acid and the crystalline compound A in the solution. The configuration of the crystalline compound A is an SS isomer in the RS notation system. The configuration of the noncrystalline compound A is an SR isomer.

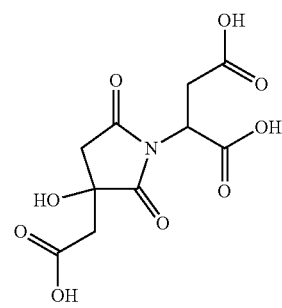

(A)

10 Claims, 9 Drawing Sheets

(56) References Cited

OTHER PUBLICATIONS

Miyake et al., "Isolation and identification of B-citryl-L-glutamic acid from newborn rat brain", Biochimica et Biophysica Acta, vol. 544, No. 3, 1978, pp. 656-666.
International Search Report issued in International Pat. Appl. No. PCT/JP2018/016495, dated Jul. 17, 2018.
International Preliminary Report on Patentability issued in International Pat. Appl. No. PCT/JP2018/016495, dated. Apr. 28, 2017.
Examination report, Australian Government, Application No. 2018259992, dated Feb. 24, 2020.
Hafer, R., Industrial Biorefineries & White Biotechnology, Elsevier (2015), p. 198.

[Fig. 1]
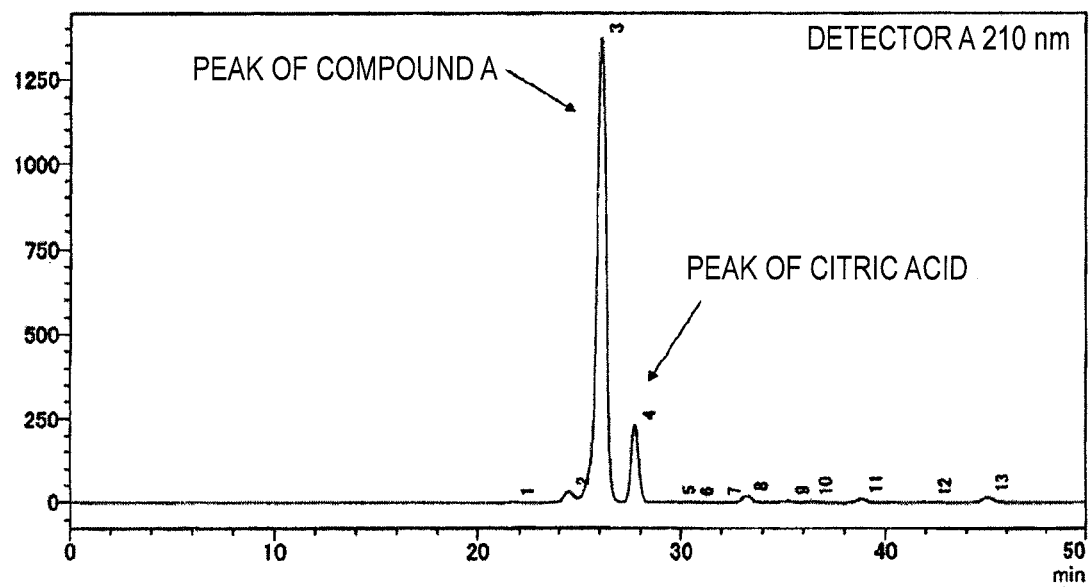
[Fig. 2]
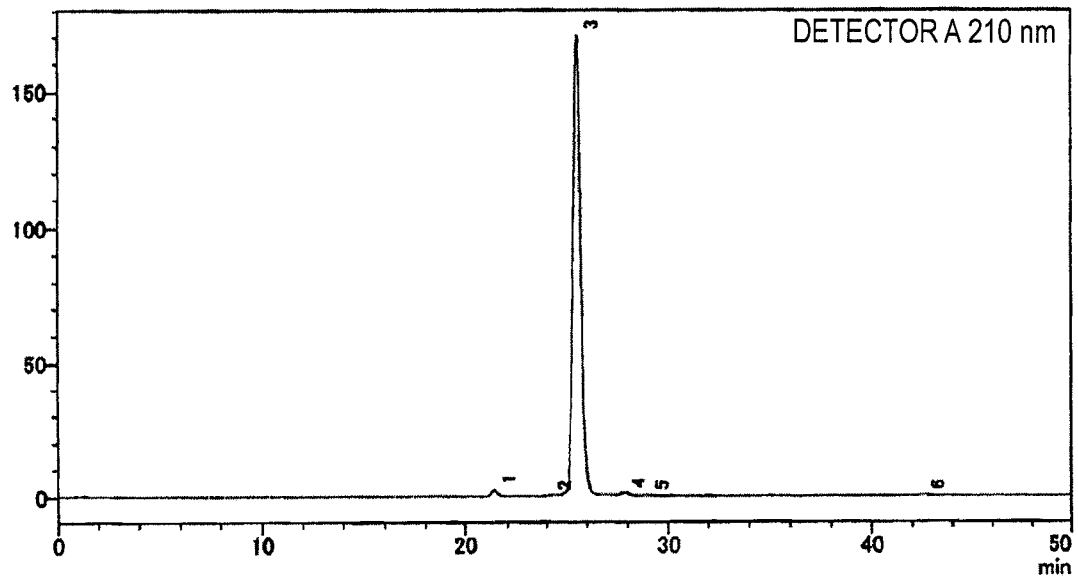

[Fig. 3]
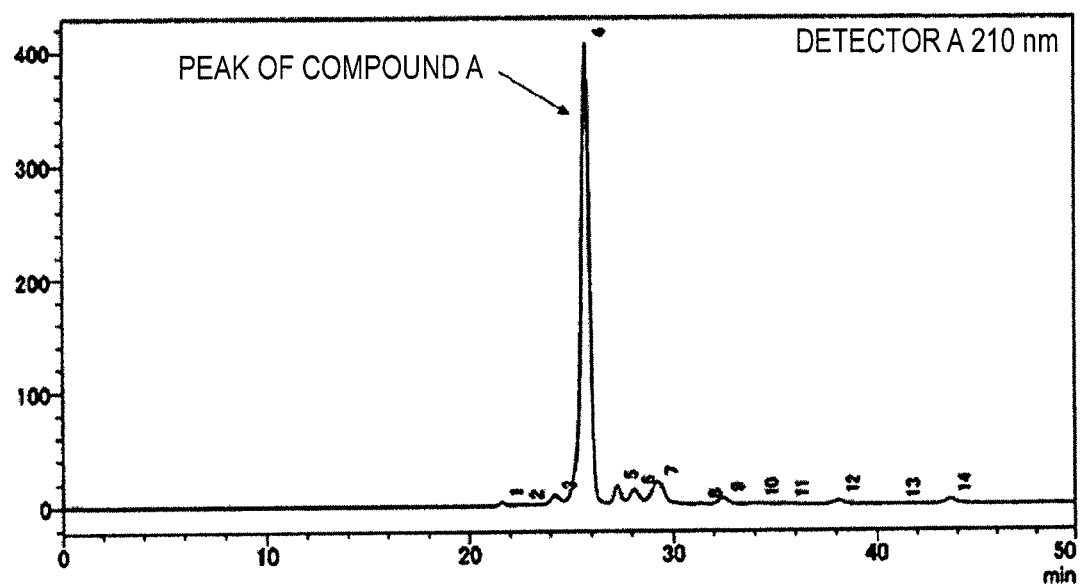
[Fig. 4]
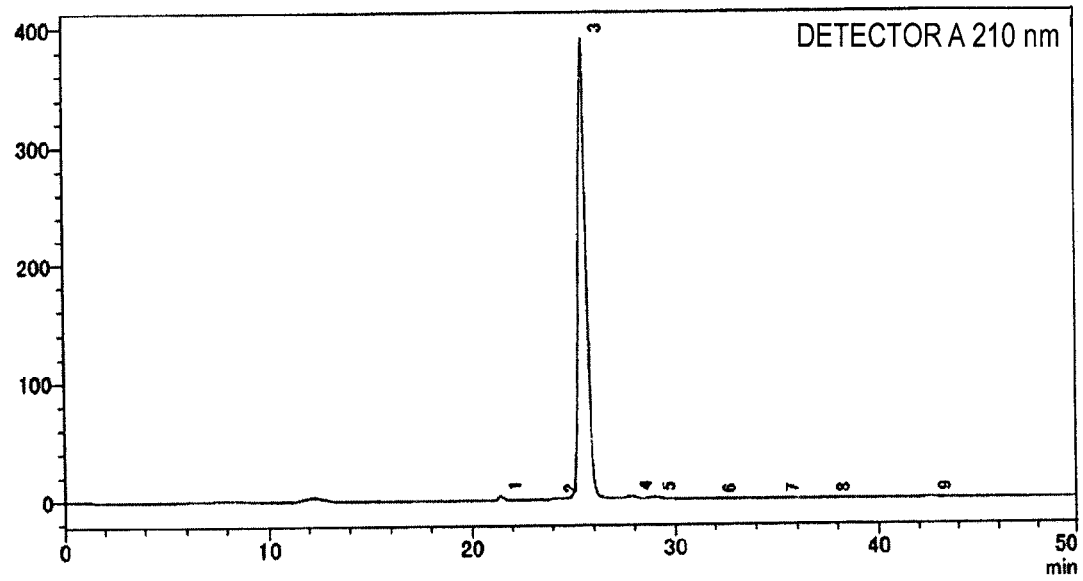

[Fig. 5]
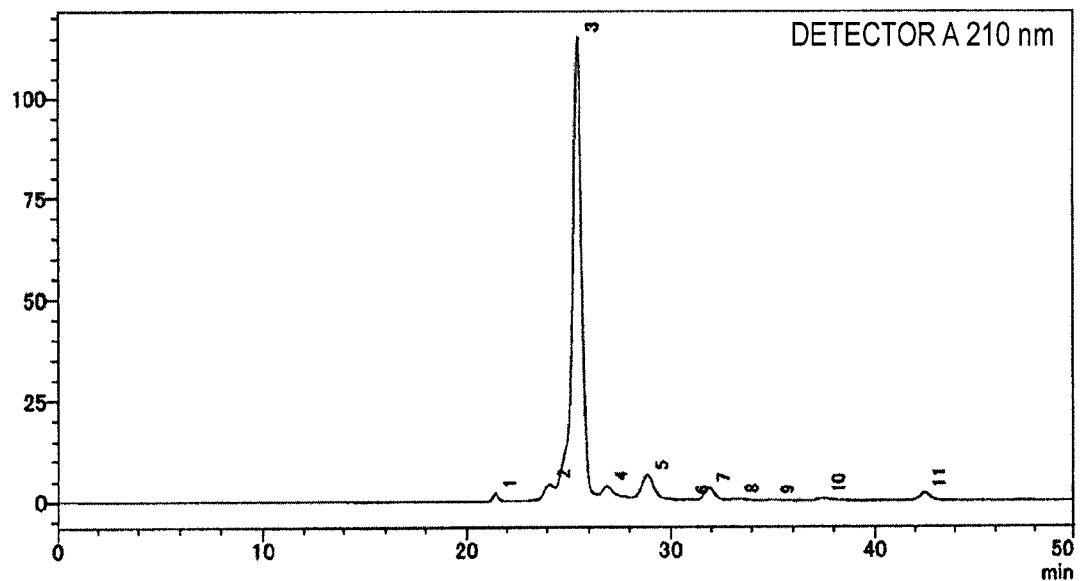
[Fig. 6]
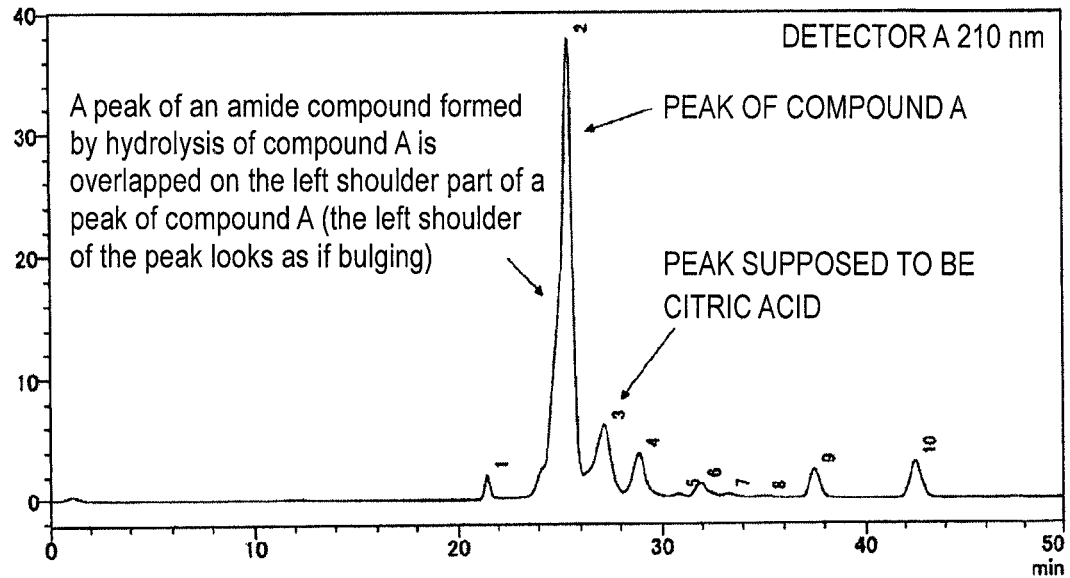

[Fig. 7]
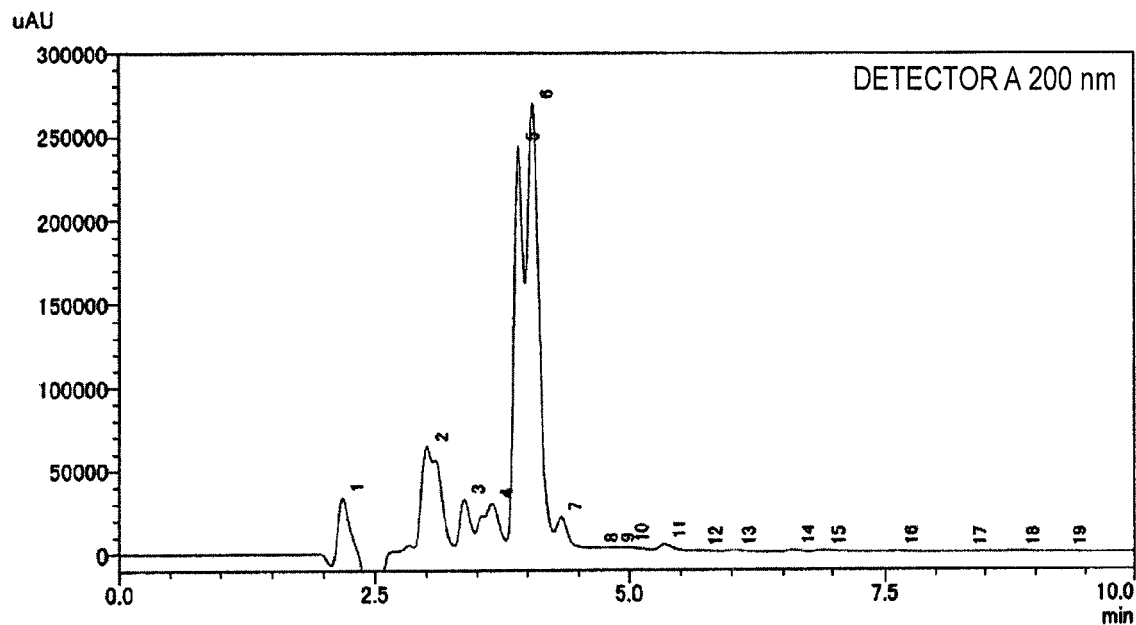
[Fig. 8]
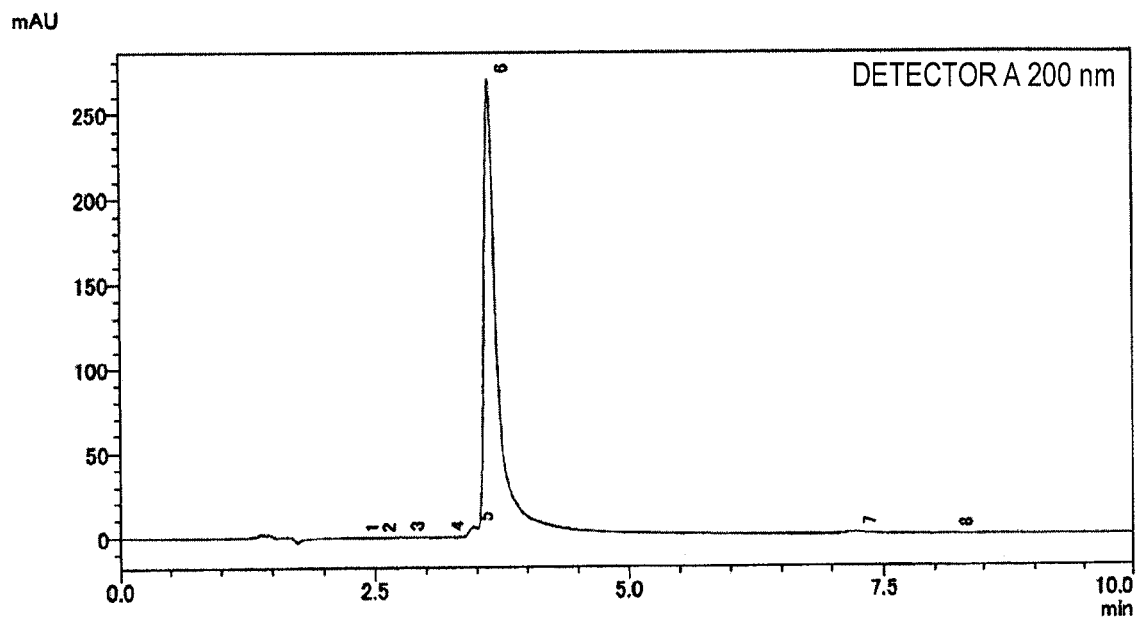

[Fig. 9]
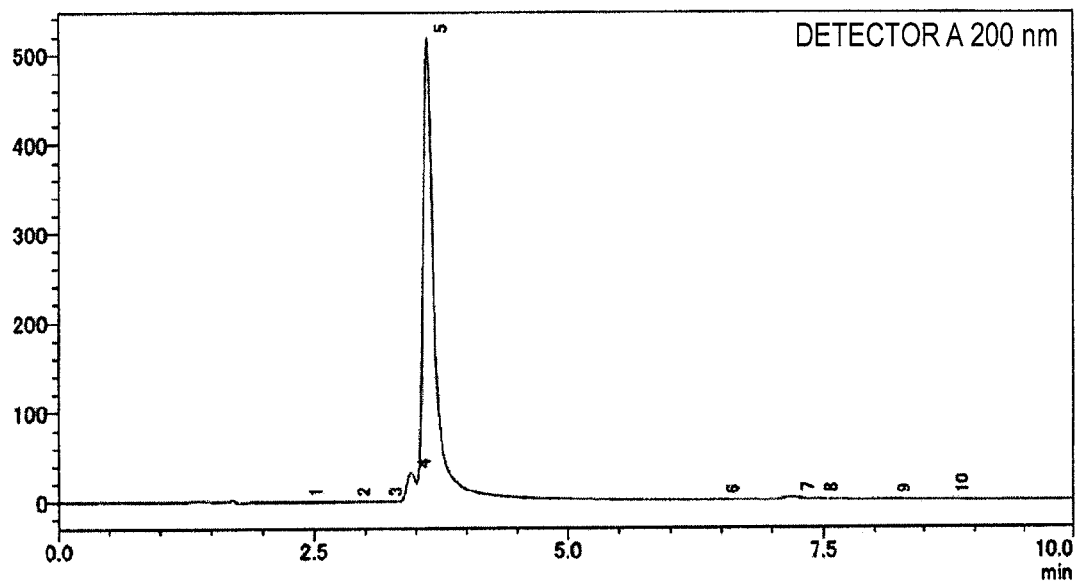
[Fig 10]
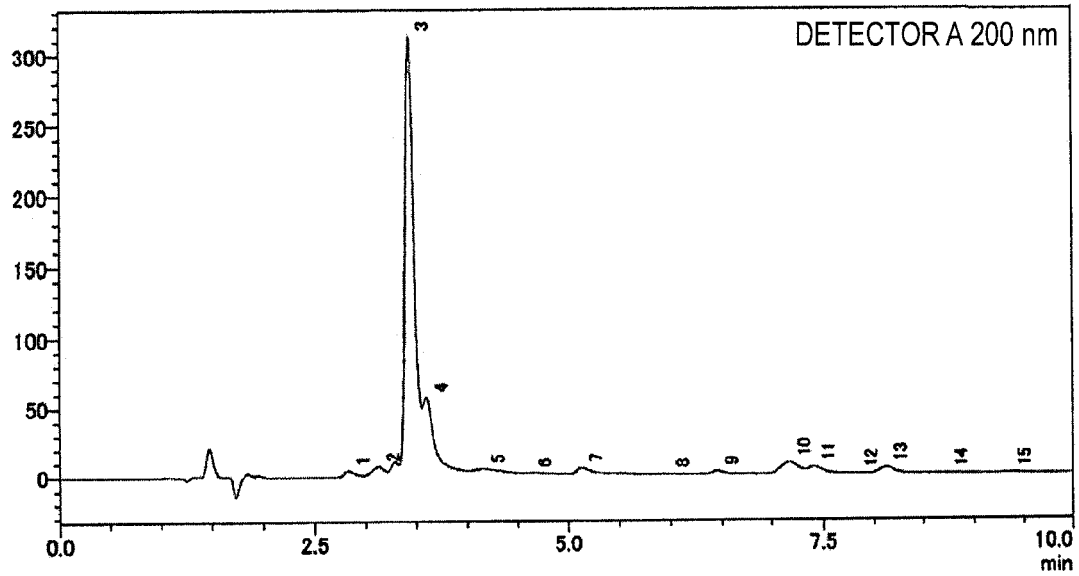

[Fig. 11]
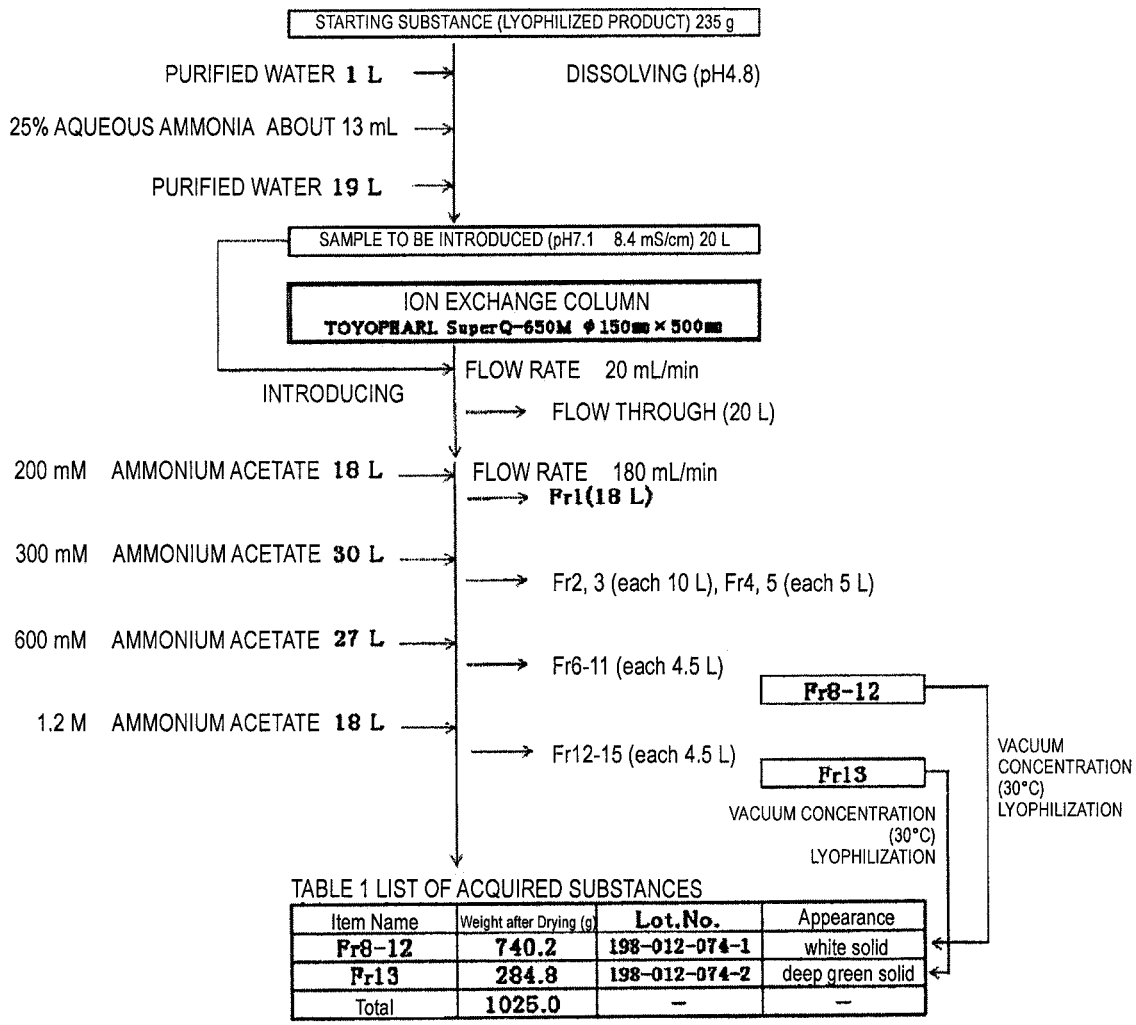

[Fig. 12]
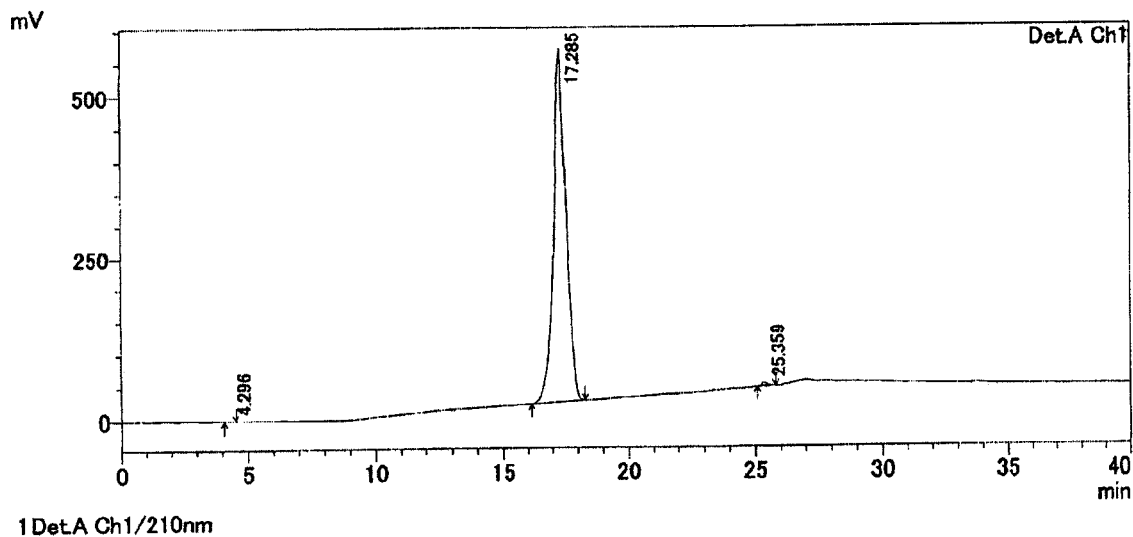
[Fig. 13]
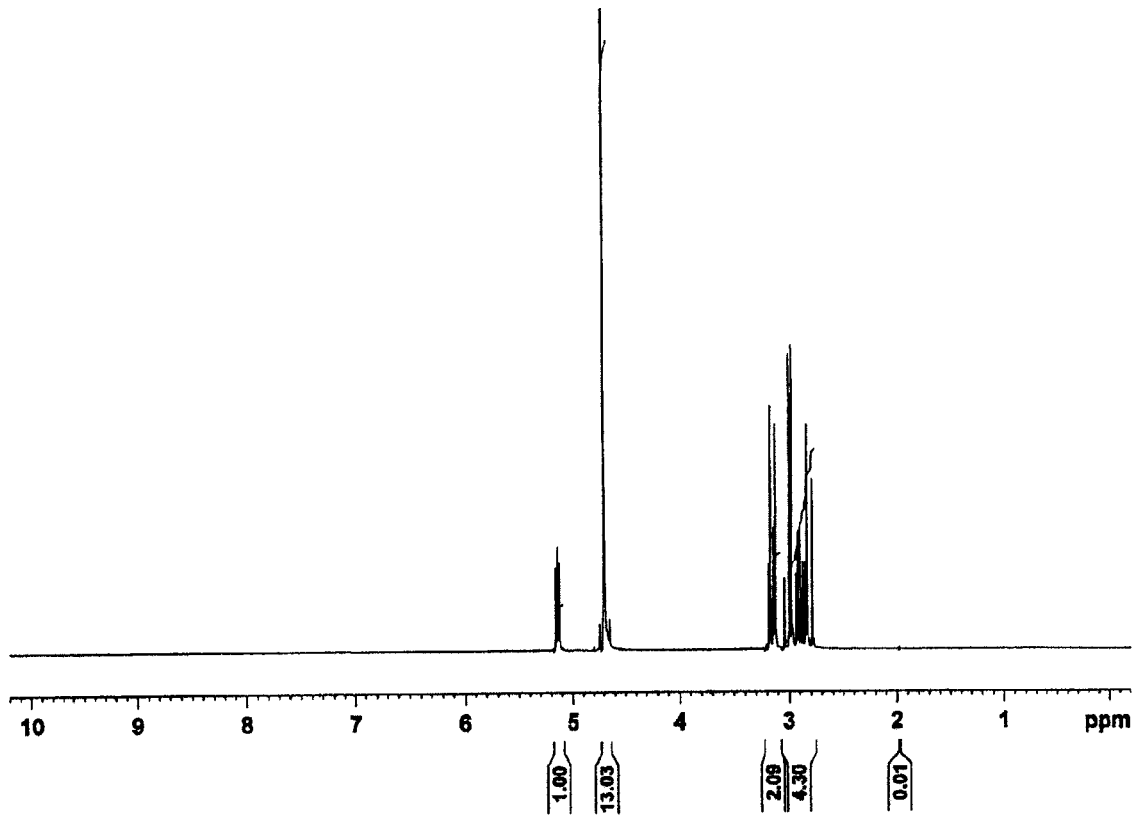

[Fig. 14]
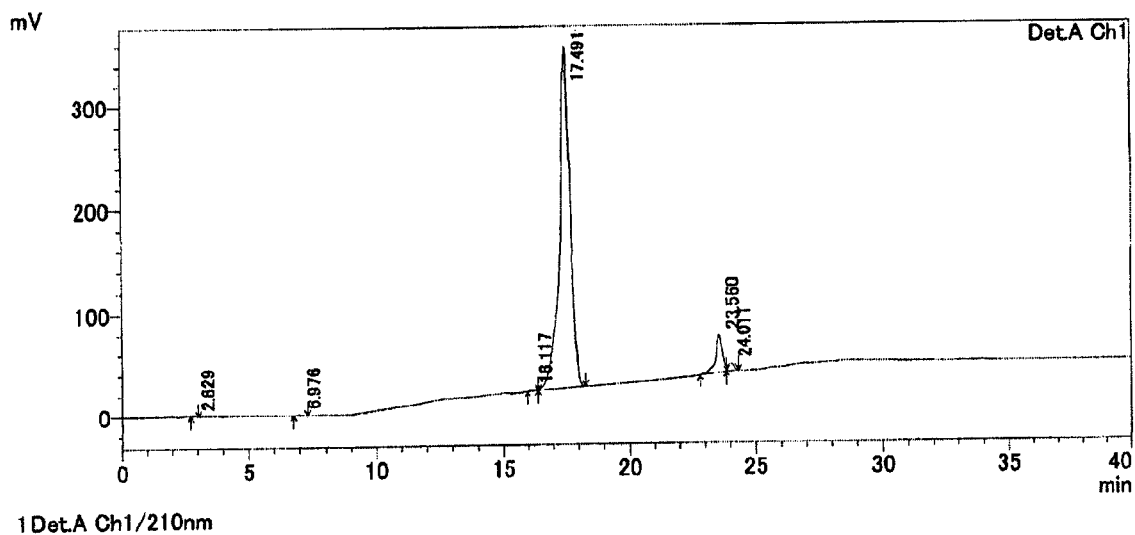
[Fig. 15]
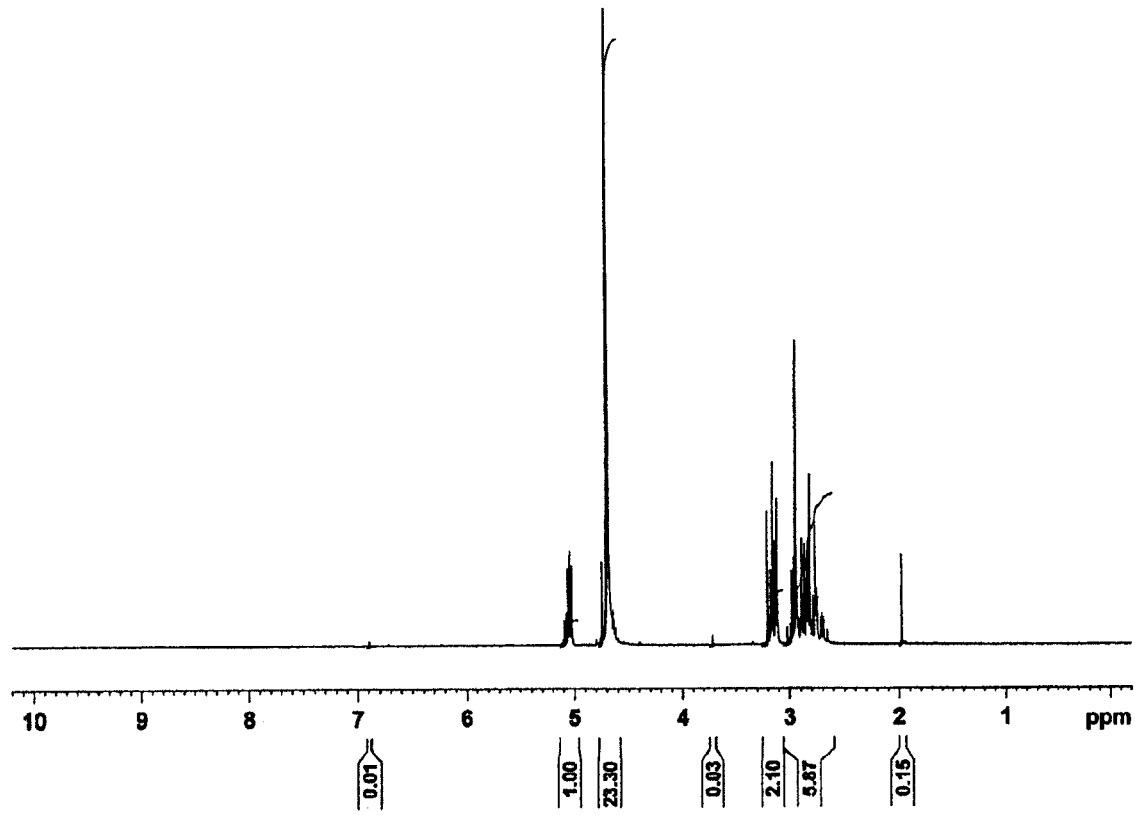

[Fig. 16]
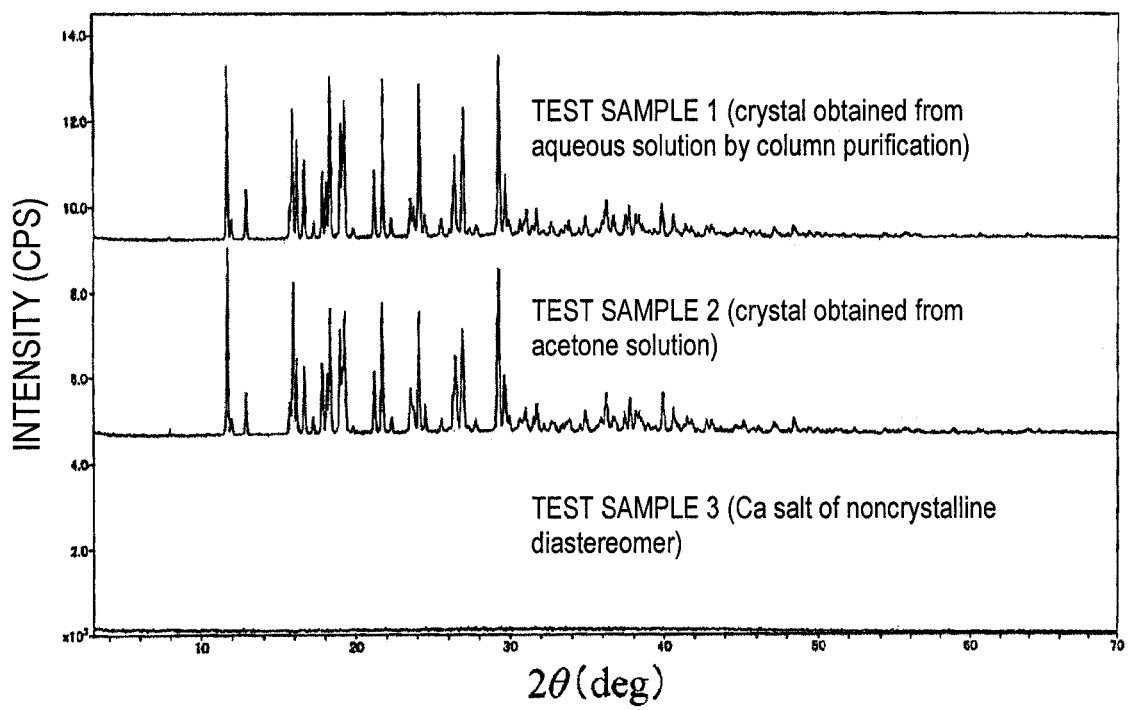

METHOD FOR MANUFACTURING DIASTEREOMER OF CITRIC ACID DERIVATIVE

TECHNICAL FIELD

The present invention relates to a crystal of a citric acid derivative having an inhibitory effect against liver disorder, a highly purified noncrystalline diastereomer (amorphous diastereomer) thereof, and their manufacturing methods.

BACKGROUND ART

Japanese apricot (ume)(scientific name: *Prunus mume*) belongs to the subgenus *Prunus* of the genus *Prunus* of the subfamily Amygdaloideae of the family Rosaceae, and is eaten as ume processed products such as pickled ume, ume liquors and ume flesh extracts. Further the ume flesh extracts have effects of disinfection, fatigue recovery, gastric protection and the like, and have been ingested for health. Further the ume flesh extracts are known to have an effect of improving bloodstream (see non-patent documents 1 and 2). The bloodstream improving effect is known to be caused by Mumefural and related compounds thereof produced by heating an organic acid such as citric acid or malic acid contained in ume flesh extract together with a sugar, (non-patent document 3).

Misatol® is commercially available as one of health foods containing ume flesh extracts, and is known to have an effect of inducing autophagy, and an inhibitory effect against liver disorder in patients with viral hepatitis (patent documents 1 and 2).

It has been found that a compound in which two carboxyl groups bound to the 1-position carbon (or 3-position carbon) and the 2-position carbon of the propane chain, which is a carbon chain of citric acid (IUPAC name: 2-hydroxypropane-1,2,3-tricarboxylic acid), form an imide bond with an amino group of a specific amino acid; and an amide compound, obtained by hydrolysis of the imide compound, of the amino acid and the carboxyl group bound to the 1-position carbon (or 3-position carbon) of the propane chain originated from citric acid are active substances having an inhibitory effect against liver disorder.

The present applicant has recently proposed, based on the above finding, a citric acid derivative comprising a compound represented by the following formula, and a synthesis method thereof (PCT/JP2016/004789).

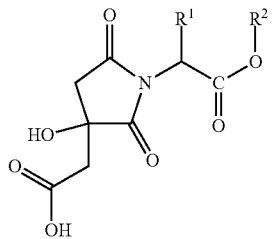

(In the formula, $R^1$ denotes a C1 to C3 alkyl group optionally having a carboxyl group or a hydroxyl group, and $R^2$ denotes a hydrogen atom; or $R^1$ and $R^2$ optionally together form a cyclic structure and denote a C2 to C3 alkylene chain.)

However, since the citric acid derivative represented by the above chemical formula having two asymmetric carbons, there exist four stereoisomers. In order to separate and acquire these stereoisomers having analogous structures, however, it is needed that a plurality of high-price columns having high separation ability are combined and the separation operation is repeated a plurality of times, and this means can attain only small amounts of separation depending on the column sizes and requires high costs. There has not been established a technology of separating and highly purifying these stereoisomers in large amounts and inexpensively.

PRIOR ART DOCUMENTS

Patent Documents

Patent Document 1: Japanese Patent No. 4842624
Patent Document 2: Japanese Patent No. 5577129

Non-Patent Documents

Non-patent Document 1: J. Agric, FoodChem., 1999, 47, 828-31
Non-patent Document 2: Journal of Hemorheology Research 1, 65-67, 1998
Non-patent Document 3: Journal of Hemorheology Research 3, 81-88, 2000

SUMMARY OF THE INVENTION

Problem to be Solved by the Invention

A problem of the present invention is to provide a method for isolating a crystalline diastereomer compound from a diastereomer mixture of a citric acid derivative, which is one among the citric acid derivative represented by the above chemical formula, represented by the following formula obtained by a reaction of citric acid with L-aspartic acid, in a large amount thereof by using inexpensive means, and a method for purifying a noncrystalline diastereomer compound from the diastereomer mixture, in a high purity in a large amount by using inexpensive means.

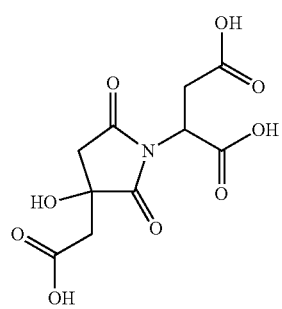 [SMILES: O=C(O)CC(C(=O)O)N1C(=O)CC(O)(CC(=O)O)C1=O]

Means to Solve the Problem

As a result of exhaustive research and studies to solve the above problem, the present inventors have found that a crystal of a compound represented by the above formula can be obtained by combining specific steps. The present inventors have also found that a noncrystalline diastereomer salt of the compound can be deposited by combining specific steps. The present inventors have also determined the structure of a crystalline diastereomer of a compound represented by the above formula by structural analysis using single-crystal X-ray diffractometry.

The present invention has been completed based on these findings.

That is, the present invention is as follows.

[1] A crystal of a compound represented by the following formula (A) (hereinafter, referred to as compound A).

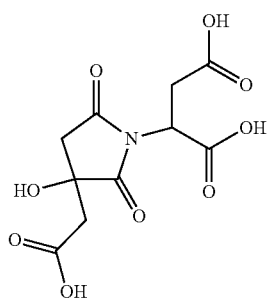

[2] The crystal according to [1], having a steric structure of an SS isomer in the RS notation system.

[3] The crystal according to [1] or [2], having peaks of diffraction angles (2θ) at 11.74±0.20°, 29.25±0.20°, 18.36±0.20°, 21.75±0.20° and 15.95±0.20° in a powder X-ray diffractometric pattern using a CuKα radiation as an X-ray source.

[4] A method for manufacturing a crystal of compound A, comprising the following steps of (a) to (f):
(a) passing an aqueous solution containing the compound A and/or a salt thereof and citric acid and/or a salt thereof and having a pH of 5.0 to 8.5 through a column packed with an anion-exchange resin;
(b) passing an eluent through the column to thereby acquire an aqueous solution containing no citric acid but containing the compound A;
(c) removing the eluent from the aqueous solution acquired by the step (b);
(d) concentrating the aqueous solution from which the eluent has been removed;
(e) water to the concentrated residue to make an aqueous solution, and concentrating the aqueous solution to thereby deposit a crystal of the compound A; and
(f) acquiring the crystal of the compound A.

[5] The manufacturing method according to [4], wherein the crystal of the compound A has a steric structure of an SS isomer in the RS notation system.

[6] The manufacturing method according to [4] or [5], wherein the eluent is an eluent selected from the group consisting of an ammonium acetate aqueous solution, a sodium chloride aqueous solution and an ammonium formate aqueous solution.

[7] The manufacturing method according to any one of [4] to [6], wherein a method of removing the eluent is a method using a column packed with a cation-exchange resin.

[8] The manufacturing method according to any one of [4] to [7], wherein a method of the concentration is lyophilization.

[9] A method for manufacturing a crystal of compound A, comprising the following steps of (a) to (f):
(a) adding calcium carbonate to an aqueous solution containing the compound A and citric acid and having a pH of 2.0 or lower to thereby deposit calcium citrate;
(b) removing calcium citrate from the 60%-methanol aqueous solution;
(c) sulfuric acid to the aqueous solution to make the pH to be 2.0 or lower to thereby deposit calcium sulfate;
(d) removing calcium sulfate from the aqueous solution;
(e) concentrating the aqueous solution to thereby deposit a crystal of the compound A; and
(f) acquiring the crystal of the compound A.

[10] The manufacturing method according to [9], wherein the crystal of the compound A has a steric structure of an SS isomer in the RS notation system.

[11] The manufacturing method according to [9] or [10], wherein the concentration is vacuum concentration.

[12] The manufacturing method according to any one of [9] to [11], further comprising, after acquiring the crystal of the compound A, the following steps of (g) to (j):
(g) adding an organic solvent to the aqueous solution to thereby deposit calcium citrate;
(h) removing calcium citrate from the mixed liquid of the aqueous solution and the organic solvent;
(i) dehydrating the mixed liquid of the aqueous solution and the organic solvent to thereby deposit a crystal of the compound A; and
(j) acquiring the crystal of the compound A.

[13] The manufacturing method according to [12], wherein the organic solvent is acetone.

[14] A method for manufacturing a noncrystalline diastereomer salt of compound A, comprising the following steps of (a) to (l):
(a) adding calcium carbonate to an aqueous solution containing the compound A and citric acid and having a pH of 2.0 or lower to thereby deposit calcium citrate;
(b) removing calcium citrate from the aqueous solution;
(c) adding sulfuric acid to the aqueous solution to make the pH to be 2.0 or lower to thereby deposit calcium sulfate;
(d) removing calcium sulfate from the aqueous solution;
(e) concentrating the aqueous solution to thereby deposit a crystal of the compound A;
(f) removing the crystal of the compound A from the aqueous solution;
(g) adding an organic solvent to the aqueous solution to thereby deposit a crystal of the compound A, and calcium citrate;
(h) removing the crystal of the compound A and calcium citrate from the mixed liquid of the aqueous solution and the organic solvent;
(i) dehydrating the mixed liquid of the aqueous solution and the organic solvent to thereby deposit a crystal of the compound A;
(j) removing the crystal of the compound A from the aqueous solution
(k) adding a metal salt or an amino acid salt and an alcohol to the aqueous solution to thereby deposit a noncrystalline diastereomer salt of the compound A; and
(l) acquiring the noncrystalline diastereomer salt of the compound A.

[15] The manufacturing method according to [14], wherein the noncrystalline diastereomer salt of the compound A has a steric structure of an SR isomer in the RS notation system.

[16] The manufacturing method according to [14], wherein the organic solvent is acetone.

[17] The manufacturing method according to any one of [14] to [16], wherein the metal salt is a metal salt selected from the group consisting of a sodium salt, a potassium salt, a magnesium salt and a calcium salt.

[18] The manufacturing method according to any one of [14] to [16], wherein the amino acid salt is an amino acid salt selected from the group consisting of an arginine salt, a citrulline salt, an ornithine salt and a histidine salt.

[19] The manufacturing method according to any one of [14] to [18], wherein the alcohol is ethanol or methanol.

[20] A noncrystalline diastereomer of compound A or a salt thereof.

[21] The noncrystalline diastereomer of compound A or a salt thereof according to [20], having a steric structure of an SR isomer in the RS notation system.

[22] The noncrystalline diastereomer of compound A or a salt thereof according to [20] or [21], wherein the salt is a metal salt or an amino acid salt of the noncrystalline diastereomer of the compound A.

[23] The noncrystalline diastereomer of compound A or a salt thereof according to [22], wherein the metal salt is a metal salt selected from the group consisting of a sodium salt, a potassium salt, a magnesium salt and a calcium salt.

[24] The noncrystalline diastereomer of the compound A or a salt thereof according to [22], wherein the amino acid salt is an amino acid salt selected from the group consisting of an arginine salt, a citrulline salt, an ornithine salt and a histidine salt.

Effect of the Invention

The acquisitions of the crystal of the compound A and the highly-purified noncrystalline diastereomer of the compound A serve to elucidate the physiological activity of the each substance and the action mechanism thereof on diseases. Further, the crystal of the compound A and the highly-purified noncrystalline diastereomer of the compound A, since being more easily handled than a diastereomer mixture containing these, are remarkably useful in manufacture or the like of medicines using the compound A as an active ingredient, or food and drink products using the compound A. Further according to the method described in the present application, the crystal of the compound A and the noncrystalline diastereomer can be separated and acquired more inexpensively in larger amounts and in a shorter time than in purifying methods using high separation columns used as common purifying means. In purifying methods using columns and the like using a high separation carrier used as usual diastereomer separating methods, the amount which can be purified in one-time purifying process depends on the column size to be used, and a large-amount purifying method using large columns which require an expensive high separation carrier is not easy in aspects of costs and efficiency. According to the method described in the present application, 20 g or more of a high-purity diastereomer can easily be separated from a 500 mL of a reaction liquid by a one-time purifying process, and the purifying scale can easily be enlarged.

BRIEF DESCRIPTION OF DRAWINGS

FIG. 1 shows an HPLC chromatogram (160-fold dilution) of a synthesis reaction liquid of the compound A.

FIG. 2 shows an HPLC chromatogram of a crystal of a compound A crystallized in an aqueous solution.

FIG. 3 shows an HPLC chromatogram of a mother solution after a crystal of the compound A has been fractionally collected.

FIG. 4 shows an HPLC chromatogram (after recrystallization) of the compound A crystallized in acetone.

FIG. 5 shows an HPLC chromatogram of a precipitate deposited at a pH of 3.6 (noncrystal compound A Ca salt (1)).

FIG. 6 shows an HPLC chromatogram of a precipitate deposited at a pH of 6.0 (noncrystal compound A Ca salt (2)). In the peak 2 in FIG. 6, a peak of an amide compound obtained by hydrolysis of the compound A is overlapped on a left shoulder part of a peak of the compound A (the left shoulder of the peak looks as if bulging). Further the peak 3 is a peak supposed to be citric acid.

FIG. 7 shows an HPLC chromatogram of a synthesis solution of a roughly purified compound A.

FIG. 8 shows an HPLC chromatogram of a crystal of the compound A crystallized in an aqueous solution (analysis result for the same sample as in FIG. 2).

FIG. 9 shows an HPLC chromatogram of the compound A crystallized in acetone (analysis result for the same sample as in FIG. 4).

FIG. 10 shows an HPLC chromatogram of the Ca salt of the noncrystalline compound A deposited at a pH of 3.6 (analysis result for the same sample as in FIG. 5).

FIG. 11 is a flow chart of a method for manufacturing a crystal of the compound A by ion exchange chromatography in Example 7.

FIG. 12 shows an HPLC chromatogram of a crystal of the compound A.

FIG. 13 shows a $^1$H-NMR spectrum of a crystal of the compound A.

FIG. 14 shows an HPLC chromatogram of a mother liquid after a crystal of the compound A has been fractionally collected.

FIG. 15 shows a $^1$H-NMR spectrum of a mother liquid after a crystal of the compound A has been fractionally collected.

FIG. 16 shows comparison by multiple plotting between powder X-ray diffractometric patterns of respective substances of a test sample 1 (a crystal obtained from an aqueous solution by column purification), a test sample 2 (a crystal obtained from an acetone solution) and a test sample 3 (a Ca salt of a noncrystalline diastereomer) in order from the top down.

MODE FOR CARRYING OUT THE INVENTION

The crystal of the compound A according to the present invention includes a crystal having peaks of diffraction angles (2θ) at 11.74±0.20°, preferably ±0.10°, 29.25±0.20°, preferably ±0.10°, 18.36±0.20°, preferably ±0.10°, 21.75±0.20°, preferably ±0.10°, and 15.95±0.20°, preferably ±0.10° in a powder X-ray diffractometric pattern using a CuKα radiation as an X-ray source.

The crystal of the compound A according to the present invention includes the crystal further having peaks of diffraction angles (2θ) at 24.09±0.20°, preferably ±0.10°, 19.32±0.20°, preferably ±0.10°, 19.04±0.20°, preferably ±0.10°, 26.95±0.20°, preferably ±0.10° and 16.19±0.20°, preferably ±0.10° in a powder X-ray diffractometric pattern using a CuKα radiation as an X-ray source, in addition to the above.

The crystal of the compound A according to the present invention includes the crystal further having, in addition to the above, peaks of diffraction angles (2θ) at 26.42±0.20°, preferably ±0.10°, 16.68±0.20°, preferably ±0.10°, 17.85±0.20°, preferably ±0.10°, 21.19±0.20°, preferably ±0.10° and 18.14±0.20°, preferably ±0.10° in a powder X-ray diffractometric pattern using a CuKα radiation as an X-ray source.

The powder X-ray diffraction patterns using CuKα as an X-ray source can be acquired by a method described in Example 8 in the present description.

The compound A has diastereomers having an asymmetric carbon as the 2-position carbon of the propane chain originated from citric acid. Here, although the compound A according to the present invention has an asymmetric carbon also in a structure originated from aspartic acid, the configuration of the asymmetric carbon is derived from aspartic acid or asparagine to be used as a raw material. The crystal of the compound A according to the present invention is derived from an L-isomer of aspartic acid.

Although the crystal of the compound A according to the present invention is a crystal of either one of diastereomers of the compound A, NMR cannot tell which one of the diastereomers the either one corresponds to.

A method of determining which diastereomer a crystal of the compound A is includes a structural analysis using single-crystal X-ray diffraction. Specifically, the method includes a method described in Example 9 as one example. As a result of the analysis in Example 9, it was clarified that a crystalline compound A (a crystal of the compound A) was enantiomers of an SS isomer and an RR isomer. Then, since aspartic acid used in the synthesis was wholly L-aspartic acid (S-isomer), it was found that the configuration of the crystalline compound A was an SS-isomer in the RS notation system.

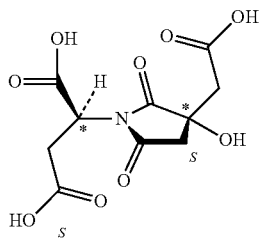

As a result of the analysis, it was clarified that the crystalline compound A was enantiomers of an SS isomer and an RR isomer. Then, since aspartic acid used in the synthesis was wholly L-aspartic acid (S-isomer), it was found that the crystalline compound A was an SS-isomer. In response to this, it was also found that the compound A having a property of not being crystallized is an SR-isomer.

The noncrystalline diastereomer of the compound A or a salt thereof according to the present invention is a diastereomer not being crystallized by a crystallization method of the compound A described in the below (hereinafter, referred to also as noncrystalline diastereomer) among diastereomers of the compound A, or a salt thereof.

The noncrystalline diastereomer of the compound A or a salt thereof according to the present invention can be confirmed by qualitative analysis using high performance liquid chromatography (HPLC) described in Example 5, and can be distinguished from the crystalline diastereomer.

As described above, since the configuration of the crystal of the compound A according to the present invention is an SS isomer in the RS notation system, it was also found that the configuration of amorphous (the noncrystalline diastereomer) of the compound A according to the present invention is an SR isomer in the RS notation system as shown below.

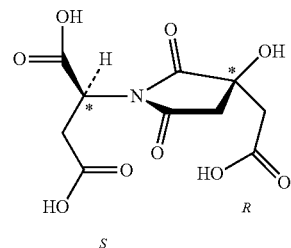

The noncrystalline diastereomer of the compound A or a salt thereof according to the present invention includes those having a mixing proportion of the crystalline diastereomer of 5% or lower, preferably 4% or lower, more preferably 3% or lower, still more preferably 2% or lower and most preferably 1% or lower.

The salt of the noncrystalline diastereomer of the compound A according to the present invention includes a metal salt and an amino acid salt.

The metal salt includes a metal salt selected from the group consisting of a sodium salt, a potassium salt, a magnesium salt and a calcium salt, and most preferably includes a calcium salt.

The amino acid salt includes an amino acid salt selected from the group consisting of an arginine salt, a citrulline salt, an ornithine salt and a histidine salt. The amino acid salt is preferably an L isomer of the amino acid salt.

The crystal of the compound A according to the present invention can be obtained by crystallization either using ion exchange column chromatography or using a compound such as calcium carbonate.

(Method Using Ion Exchange Column Chromatography)

The crystal of the compound A is manufactured by the following steps of (a) to (f):

(a) passing an aqueous solution containing the compound A and/or a salt thereof and citric acid and/or a salt thereof and having a pH of 5.0 to 8.5 through a column packed with an anion-exchange resin;

(b) passing an eluent through the column to thereby acquire an aqueous solution containing no citric acid but containing the compound A;

(c) removing the eluent from the aqueous solution acquired by the step (b);

(d) concentrating the aqueous solution from which the eluent has been removed;

(e) adding water to the concentrated residue to make an aqueous solution, and concentrating the aqueous solution to thereby deposit a crystal of the compound A; and (f) acquiring the crystal of the compound A.

There are not especially limited the salt of the compound A and the salt of citric acid in the aqueous solution containing the compound A and/or a salt thereof and citric acid and/or a salt thereof and having a pH of 5.0 to 8.5. Examples of the salt of the compound A and the salt of citric acid include an amino acid salt and a metal salt (a sodium salt, a potassium salt, a magnesium salt, a calcium salt). Most preferable as the compound A and/or a salt thereof and citric acid and/or a salt thereof are the compound A and citric acid.

The aqueous solution containing the compound A and/or a salt thereof and citric acid and/or a salt thereof and having a pH of 5.0 to 8.5, to be used in the above step (a) is manufactured, for example, as follows. Citric acid monohydrate and L-aspartic acid are reacted under heating to thereby form a compound A. The compound A may be a compound A manufactured by a method other than the synthesis method, such as an enzyme reaction method or a fermentation method. After completion of the reaction, the reaction liquid is allowed to cool, and methanol is added in an acidic condition. The concentration of the methanol solution may be any concentration as long as being a concentration at which L-aspartic acid deposits, but is, for example, 60 V/V %. Since out of unreacted citric acid and L-aspartic acid contained in the reaction liquid, the L-aspartic acid deposits and precipitates, the deposit and precipitate is solid-liquid separated by centrifugal separation or filtration. The aqueous solution after the solid-liquid separation contains the compound A and citric acid. In the case where the aqueous solution after the solid-liquid separation is acidic, it is preferable that an alkali aqueous solution, for example, an aqueous ammonia, is added to adjust the pH. The pH of the aqueous solution is 5.0 to 8.5, preferably 6.0 to 8.0 and most preferably 6.5 to 7.2. The aqueous solution is passed through a column packed with an anion-exchange resin.

The anion-exchange resin may be any anion-exchange resin capable of separating the compound A and/or a salt thereof and citric acid and/or a salt thereof, but examples thereof include a TOYOPEARL SuperQ-650M (150 mm×500 mm, manufactured by Tosoh Corp.).

An eluent to be used in the above step (b) is not especially limited, but is selected, for example, from the group consisting of an ammonium acetate aqueous solution, a sodium chloride aqueous solution and an ammonium formate aqueous solution.

The concentration of the eluent is 50 mM to 5M, preferably 100 mM to 3M, more preferably 150 mM to 2M and most preferably 200 mM to 1.5M. The elution may be carried out by stepwise raising the concentration of the eluent.

The flow rate of the elution step is in the range of 10 to 500 mL/min, preferably 50 to 300 mL/min and most preferably 100 to 200 mL/min.

It is desirable that "containing no citric acid" in the above step (b) is not containing any citric acid, but a tiny amount of citric acid may be contained to the extent of not becoming an obstacle in crystallization of the compound A.

In the above step (c), examples of a method of removing the eluent include a method using a column packed with a cation-exchange resin, and electrodialysis, and preferably include the method using a column packed with a cation-exchange resin. Here, "removing the eluent" means removing components (solutes) in the eluent.

The cation-exchange resin may be any cation-exchange resin as long as being capable of separating the compound A and the eluent, but includes a DOWEX 50Wx8 (manufactured by Wako Chemical Corp.). By feeding an aqueous solution, for example, purified water, to a column packed with the cation-exchange resin, there is acquired an aqueous solution containing the compound A but containing no eluent. It is desirable that "containing no eluent" is not containing any eluent, but a tiny amount of the eluent may be contained to the extent of not becoming an obstacle in crystallization of the compound A.

In the above steps (d) and (e), methods of concentrating the aqueous solutions include heating concentration, vacuum concentration and lyophilization, and most preferably include lyophilization.

In the above steps (d) and (e), by concentrating the aqueous solutions, there can be acquired a noncrystal and/or a crystal of the compound A, or a mixture thereof, or a concentrated residue containing these. In the case where compound A is a noncrystal, in the case of being a mixture containing the noncrystal, or in the case of being a concentrated residue containing these, it is preferable that water is again added to make a water mixture and a concentration step is carried out. By carrying out this step, a crystal of the compound A can be deposited.

In the above step (f), a method of acquiring the crystal includes pressure filtration, suction filtration and centrifugal separation. Further in order to reduce adhesion of a mother liquid and improve the quality of the crystal, the crystal can suitably be washed. The washed crystal is dried by vacuum drying, fluidized-bed drying, forced-air drying or the like to thereby obtain the final product.

In the above method, the crystallization of the compound A can be attained also by carrying out the step (d) and the step (e) repeatedly several times.

(Method by Crystallization Using a Compound Such as Calcium Carbonate)

A crystal of the compound A is manufactured in an aqueous solution by the following steps of (a) to (f):

(a) adding calcium carbonate to an aqueous solution containing the compound A and citric acid and having a pH of 2.0 or lower to thereby deposit calcium citrate;
(b) removing calcium citrate from the aqueous solution;
(c) adding sulfuric acid to the aqueous solution to make the pH to be 2.0 or lower to thereby deposit calcium sulfate;
(d) removing calcium sulfate from the aqueous solution;
(e) concentrating the aqueous solution to thereby deposit a crystal of the compound A; and
(f) acquiring the crystal of the compound A.

The aqueous solution containing the compound A and citric acid and having a pH of 2.0 or lower, to be used in the above step (a) is manufactured, for example, as follows. Citric acid monohydrate and L-aspartic acid are reacted under heating to thereby form a compound A. The compound A may be a compound A manufactured by a method other than the synthesis method, such as an enzyme reaction method or a fermentation method. After completion of the reaction, the reaction liquid is allowed to cool, and methanol is added in an acidic condition. The concentration of the methanol solution may be any concentration as long as being a concentration at which L-aspartic acid deposits, but is, for example, 60 v/v %. Since out of unreacted citric acid and L-aspartic acid contained in the reaction liquid, the L-aspartic acid deposits and precipitates, the deposit and precipitate is solid-liquid separated by centrifugal separation. Here, in this step, the addition of methanol is important. Ethanol is not allowed. For subsequent steps, the aqueous solution after the solid-liquid separation containing the compound A and citric acid is used.

The difficult point when the crystal of the compound A is obtained by the present method is in removing citric acid from the aqueous solution containing the compound A and citric acid in an acidic condition. Since the compound A is unstable in a neutral to alkaline (pH of 5 or higher) aqueous solution, in order to suppress decomposition of the compound A, maintenance of an acidic condition is important. Therefore, the aqueous solution containing the compound A and citric acid and having a pH of 2.0 or lower to be used in the step (a) may be an aqueous solution whose pH is preferably 0.6 to 1.8 and most preferably 1.0 to 1.6. The present inventors have thought of removing citric acid by turning it into a form of a salt, and as a result of repeating trial and error using salts consisting of various metal ions, have found that use of calcium ion ($Ca^{2+}$) can well remove citric acid. The present inventors have further also found that even if the salt is a calcium salt, in the case of using calcium chloride ($CaCl_2$), citric acid cannot be removed well in an acidic condition, and in the case of using calcium carbonate ($CaCO_3$), citric acid can successfully be removed even in an acidic condition. This is conceivably because since carbonate ions ($CO_3^{2-}$) of calcium carbonate turn to $CO_2$ and anions as counter ions of calcium ions disappear, it becomes easy for citric ions and calcium ions to be bound. Therefore, use of calcium carbonate in the step (a) is an essential condition.

The removal of calcium citrate in the above step (b) and the removal of calcium sulfate in the above step (d) can be carried out, for example, by centrifugal separation or filtration.

The reason of using sulfuric acid in the above step (c) includes that due to frailty to alkali of the compound A and lowness in solubility of calcium sulfate, removal of calcium ions is easy (that is, desalting is easy). By making the pH to be 2.0 or lower, calcium ions present as a calcium salt of the compound A dissociate from the compound A and become calcium sulfate. The pH at this time is preferably 1.0 to 2.0 and more preferably 1.3 to 1.8. In the case of using a sodium salt (sodium sulfate) or a potassium salt (potassium sulfate), the desalting is difficult.

Specific examples of a method of concentrating the aqueous solution in the above step (e) include heating concentration and vacuum concentration, but in order to prevent deterioration or decomposition of mixed components by heat, use of vacuum concentration is preferable.

In the above step (f), a method of acquiring the crystal includes pressure filtration, suction filtration and centrifugal separation. Further in order to reduce adhesion of a mother liquid and improve the quality of the crystal, the crystal can suitably be cleaned. The cleaned crystal is dried by vacuum drying, fluidized-bed drying, forced-air drying or the like to thereby obtain the final product.

In the aqueous solution (crystal mother liquid) after the crystal of the compound A is deposited in the above step (e), a crystalline compound A diastereomer is still contained. Hence, the crystal of the compound A can further be obtained by carrying out the following steps of (g) to (j):
(g) adding an organic solvent to the aqueous solution to thereby deposit calcium citrate;
(h) removing calcium citrate from the mixed liquid of the aqueous solution and the organic solvent;
(i) dehydrating the mixed liquid of the aqueous solution and the organic solvent to thereby deposit a crystal of the compound A; and
(j) acquiring the crystal of the compound A.

The organic solvent to be added in the above step (g) is preferably an organic solvent which is miscible with water and can dissolve a certain amount of the compound A, and specific examples thereof include acetone.

The removal of calcium citrate in the above step (h) can be carried out, for example, by centrifugal separation or filtration.

A method of depositing the crystal of the compound A in the above step (i) may be any method of depositing the compound, but preferably includes a method in which the aqueous solution is concentrated by solvent distilling-away and a solvent is again added.

In the above step (j), a method of acquiring the crystal includes pressure filtration, suction filtration and centrifugal separation. Further in order to reduce adhesion of a mother liquid and improve the quality of the crystal, the crystal can suitably be cleaned. The cleaned crystal is dried by vacuum drying, fluidized-bed drying, forced-air drying or the like to thereby obtain the final product.

The noncrystalline diastereomer salt of the compound A according to the present invention can be obtained by a method comprising the following steps of (a) to (l):
(a) adding calcium carbonate to an aqueous solution containing the compound A and citric acid and having a pH of 2.0 or lower to thereby deposit calcium citrate;
(b) removing calcium citrate from the aqueous solution;
(c) adding sulfuric acid to the aqueous solution to make the pH to be 2.0 or lower to thereby deposit calcium sulfate;
(d) removing calcium sulfate from the aqueous solution;
(e) concentrating the aqueous solution to thereby deposit a crystal of the compound A;
(f) removing the crystal of the compound A;
(g) adding an organic solvent to the aqueous solution to thereby deposit a crystal of the compound A and calcium citrate;
(h) removing the crystal of the compound A and calcium citrate from the mixed liquid of the aqueous solution and the organic solvent;
(i) dehydrating the mixed liquid of the aqueous solution and the organic solvent to thereby deposit a crystal of the compound A;
(j) removing the crystal of the compound A from the aqueous solution;
(k) adding a metal salt or an amino acid salt and an alcohol to the aqueous solution to thereby deposit a noncrystalline diastereomer salt of the compound A; and
(l) acquiring the noncrystalline diastereomer salt of the compound A.

The aqueous solution containing the compound A and citric acid and having a pH of 2.0 or lower, to be used in the above step (a) is manufactured, for example, as follows. Citric acid monohydrate and L-aspartic acid are reacted under heating to thereby form a compound A. The compound A may be a compound A manufactured by a method other than the synthesis method, such as an enzyme reaction method or a fermentation method. After completion of the reaction, the reaction liquid is allowed to cool, and methanol is added in an acidic condition. The concentration of the methanol solution may be any concentration as long as being a concentration at which L-aspartic acid deposits, but is, for example, 60 v/v %. Since out of unreacted citric acid and L-aspartic acid contained in the reaction liquid, the L-aspartic acid deposits and precipitates, the deposit and precipitate is solid-liquid separated by centrifugal separation. Here, in this step, the addition of methanol is important. Ethanol is not allowed. For subsequent steps, there is used the aqueous solution after the solid-liquid separation containing the compound A and citric acid. The aqueous solution containing the compound A and citric acid and having a pH of 2.0 or lower may be an aqueous solution whose pH is preferably 0.6 to 1.8 and most preferably 1.0 to 1.6.

The difficult point when the crystal of the compound A is obtained by the present method is in removing citric acid from the aqueous solution containing the compound A and citric acid. The present inventors have thought of removing citric acid by turning it into a form of a salt, and as a result of repeating trial and error using salts consisting of various metal ions, have found that use of calcium ion ($Ca^{2+}$) can well remove citric acid. The present inventors have further also found that even if the salt is a calcium salt, in the case of using calcium chloride ($CaCl_2$), citric acid cannot be removed well in an acidic condition, and in the case of using calcium carbonate ($CaCO_3$), citric acid can successfully be removed even in an acidic condition. This is conceivably because since carbonate ions ($CO_3^{2-}$) of calcium carbonate turn to $CO_2$ and anions as counter ions of calcium ions disappear, it becomes easy for citric ions and calcium ions to be bound. Therefore, use of calcium carbonate in the step (a) is an essential condition.

The removal of calcium citrate in the above step (b) and the removal of calcium sulfate in the above step (d) can be carried out, for example, by centrifugal separation or filtration.

The reason of using sulfuric acid in the above step (c) includes that due to frailty to alkali of the compound A and lowness in solubility of calcium sulfate, removal of calcium ions is easy (that is, desalting is easy). By making the pH to be 2.0 or lower, calcium ions present as a calcium salt of the compound A dissociate from the compound A and become calcium sulfate. The pH at this time is preferably 1.0 to 2.0 and more preferably 1.3 to 1.8. In the case of using a sodium salt (sodium sulfate) or a potassium salt (potassium sulfate), the desalting is difficult.

Specific examples of a method of concentrating the aqueous solution in the above step (e) include heating concentration and vacuum concentration, but in order to prevent deterioration or decomposition of mixed components by heat, use of vacuum concentration is preferable.

In the above step (f), a method of removing the crystal includes pressure filtration, suction filtration and centrifugal separation.

The above step (g) and step (h) are steps essential for high purification of the diastereomer salt of the compound A. The reason therefor is because in the aqueous solution after the crystal of the compound A has been removed in the step (f), the compound A to be still crystallized remains.

The organic solvent to be added in the above step (g) is preferably an organic solvent which is miscible with water and can dissolve a certain amount of the compound A, and specific examples thereof include acetone.

The removal of calcium citrate in the above step (h) can be carried out, for example, by centrifugal separation or filtration.

A method of depositing the crystal of the compound A in the above step (i) may be any method of depositing the compound, but preferably includes a method in which the aqueous solution is concentrated by solvent distilling-away and a solvent is again added.

In the above step (j), a method of removing the crystal includes centrifugal separation, pressure filtration and suction filtration. In the stage of the above step (j), the crystalline compound A is practically removed.

The metal salt to be added in the above step (k) includes a sodium salt, a potassium salt, a magnesium salt and a calcium salt, and most preferably, a calcium salt (as an example, calcium chloride or calcium acetate) can be used. Then the pH of the aqueous solution is preferably acidic and most preferably 3.6 or lower.

The amino acid salt to be added in the above step (k) includes an amino acid selected from the group consisting of an arginine salt, a citrulline salt, an ornithine salt and a histidine salt, and examples thereof include an L-arginine hydrochloride, an L-citrulline hydrochloride, an L-ornithine hydrochloride and an L-histidine hydrochloride.

The alcohol to be added in the above step (k) includes methanol, ethanol, n-propanol and isopropanol, and there can be used, for example, ethanol or methanol. The efficiency of depositing the diastereomer salt of the compound A is better in the case of ethanol than in the case of methanol.

The compound A according to the present invention can be synthesized by using, as starting substances, citric acid and L-aspartic acid and/or L-asparagine (most preferably L-aspartic acid). In this case, the synthesized compound A consists of a mixture of two diastereomers. According to the following procedure, crystallization of the compound A and deposition of the noncrystalline diastereomer salt of the compound A can be carried out continuously. Here, in the following steps, conditions of the corresponding steps described above may be used.

(1) Citric acid monohydrate and L-aspartic acid and/or L-asparagine (most preferably L-aspartic acid) are reacted under heating to thereby form the compound A. The heating temperature and the reaction time can be determined in consideration of various conditions (for example, 121° C., 8 hours).

(2) After completion of the reaction, the reaction liquid is allowed to cool, and methanol (for example, 60% methanol solution) is added in an acidic condition. Since out of unreacted citric acid and L-aspartic acid contained in the reaction liquid, L-aspartic acid deposits and precipitates, the deposit and precipitation is solid-liquid separated by centrifugal separation or filtration. The separated L-aspartic acid can be reutilized. Here, in this step, although even if ethanol or isopropanol, other than methanol, is added, L-aspartic acid can be removed, methanol is most suitable from the viewpoint of solubility of calcium carbonate to be added later.

(3) Purified water is added to the methanol solution containing the obtained compound A and citric acid for dilution (for example, two-fold dilution), and then a calcium carbonate powder (for example, 228 mg per 1 mL of the reaction liquid) is added. Thereby, the reaction liquid is foamed and calcium citrate is precipitated. The precipitated calcium citrate is solid-liquid separated by centrifugal separation or filtration. The reaction liquid from which calcium citrate has been removed is a methanol solution of the compound A containing calcium ions.

(4) The reaction liquid obtained in (3) is concentrated to distil methanol away, and purified water is added to make the volume of the reaction liquid to be equal to that of the initial reaction liquid. For example, 1 M sulfuric acid is added thereto to make the pH to be 2.0 or lower and 1.3 or higher, so that calcium ions become calcium sulfate, which is then precipitated. The precipitated calcium sulfate is solid-liquid separated by centrifugal separation or filtration. The reaction liquid after the solid-liquid separation is a sulfuric acid acidic solution containing the compound A.

(5) By concentrating the sulfuric acid acidic solution, for example, to about 2/5, since a crystal of the compound A (referred to as "crystallized compound A") is crystallized, the crystal is separated and the rest is treated as a crystal mother liquid.

(6) By concentrating the sulfuric acid-acidic crystal mother liquid, and adding acetone to make an acetone solution (acidic) (for example, 80% acetone solution) of the compound A, a viscous precipitate is deposited and later crystallized (calcium citrate). The calcium citrate is solid-liquid separated by centrifugal separation or filtration.

(7) The crystal mother liquid after the solid-liquid separation is concentrated and dehydrated (dehydration in acetone). By adding acetone to the crystal mother liquid after the dehydration so that acetone in the solvent is made to be, for example, 90% or higher, the compound A is crystallized and precipitated. The crystallized compound A (referred to as "crystallized compound A") is solid-liquid separated by centrifugal separation or filtration.

(8) Purified water is added to the acetone solution of the compound A, and acetone is distilled away. Calcium chloride and calcium hydroxide are added to the aqueous solution of the compound A after the distilling-away of acetone so that the pH becomes, for example, 3.6; and then by adding ethanol (for example, 70% ethanol aqueous solution), a calcium salt of a noncrystalline diastereomer of the compound A is precipitated. The precipitate (referred to as noncrystal compound A (Ca salt)) is solid-liquid separated by centrifugal separation or filtration.

The crystallized compound A (crystal in the aqueous solution) obtained in the above step (5) and the crystallized compound A (crystal in acetone) obtained in the above step (7) are each stored by being subjected to the following operation.

Redissolving in water→recrystallizing→purity evaluation by qualitative analysis using HPLC→drying→storing The noncrystal compound A (Ca salt) obtained in the above step (8) is stored by being subjected to the following operation.

Redissolving in water→concentrating (removing precipitated calcium citrate)→adding ethanol (for example, 90v/v % ethanol aqueous solution) to the aqueous solution of the compound A→re-precipitating→purity evaluation by qualitative analysis using HPLC→drying→storing With regard to the obtained noncrystal compound A (Ca salt), in use thereof, by making it to be acidic with sulfuric acid, calcium can be removed therefrom and the concentration as the compound A can be evaluated by qualitative and quantitative analysis using HPLC.

EXAMPLES

Hereinafter, the present invention will be described specifically by way of Examples, but the present invention is in no way limited thereto.

Example 1

(Synthesis of the Compound A)

Water was added to 240 g (1.142 mol) of citric acid (monohydrate, Wako Pure Chemical Industries, Ltd.) to prepare 400 mL of a thick citric acid solution; 72 g (0.541 mol) of L-aspartic acid (Wako Pure Chemical Industries, Ltd.) was added to the solution; and the resultant solution was diluted to a solution volume of 600 mL (citric acid final concentration: 1.903 mol/L, L-aspartic acid final concentration: 0.902 mol/L). The reaction liquid was put in a pressure-resistant glass vessel and sealed therein, and heated in a water bath at 90° C. to thereby dissolve as much of the L-aspartic acid added as possible. Then, the reaction liquid in the pressure-resistant vessel was put in an autoclave heated at about 80° C., and heat treated at 121° C. for 120 min. The temperature in the autoclave was lowered to about 80° C., and the reaction liquid in the pressure-resistant vessel was taken out and stirred to thereby dissolve as much of the L-aspartic acid remaining undissolved as possible. The reaction liquid was further heat treated in the autoclave at 121° C. for 120 min. The stirring and the heat treatment were repeated to carry out the heat treatment at 121° C. for the total of 420 min while L-aspartic acid was dissolved. (The L-aspartic acid was completely dissolved at the time when the heating for the total of 360 min finished.) It was confirmed by qualitative analysis using HPLC described in the following Example 2 that the compound A was synthesized in the reaction liquid (FIG. 1). FIG. 1 shows an HPLC chromatogram (160-fold dilution) of the compound A synthesis reaction liquid. As is clear from FIG. 1, with regard to the synthesis reaction liquid after the heat reaction, a peak (RT 26.0) of the compound A emerged and the height of a peak (RT 27.7) of citric acid reduced. Here, it was confirmed by subsequent analysis that the peak at RT 26.0 was the compound A. Here, the aspartic acid as a synthesis raw material, since exhibiting almost no light absorption at 210 nm, was not detected by a detection system in here.

Example 2

(Separation Condition in Qualitative Analysis Using HPLC of the Compound A)

With regard to the compound A present in the synthesis reaction liquid and a purified sample thereof, the presence of the compound A was confirmed by qualitative analysis using the following high performance liquid chromatography (HPLC). Solutions having various concentrations of the compound A were diluted with a 10 mM perchloric acid aqueous solution (mobile phase for qualitative analysis using HPLC) so as to have a suitable concentration; undissolved substances were removed by a membrane filter; and the diluted solution was analyzed by high performance liquid chromatography. The separation condition in qualitative analysis using HPLC was as follows. The title component supposed to be the compound A in the chromatogram had a peak at a retention time (RT) of 25.4 to 26.0 min.

[Separation Condition in Qualitative Analysis Using HPLC]
Apparatus: Shimadzu Corp., high performance liquid chromatograph Prominence
Columns: two coupled columns, Shodex RSpak KC-811 (300 mm×8.0 mm)
Mobile phase: 10 mM perchloric acid aqueous solution
Flow rate: 0.5 mL/min
Column temperature: 30° C.
Injection volume: 20 µL
Detection wavelength: 210 nm Example 3

(Purification of the Compound A and Crystallization of the Compound A)

When 900 mL of methanol (Wako Pure Chemical Industries, Ltd.) was added to 600 mL of the reaction liquid after the heat reaction to make a 60% methanol solution, unreacted L-aspartic acid in the reaction liquid gradually deposited and precipitated as a white precipitate. Here, in the case of using an ethanol solution in this step, even if the similar steps were adopted in subsequent steps, the compound A was not crystallized. The solution was allowed to stand for a whole day and night at room temperature to precipitate as much of L-aspartic acid as possible, and thereafter filtered with a filter paper (Whatman plc, No. 114) to thereby separate a precipitate and the reaction liquid (60% methanol) containing the compound A. The L-aspartic acid obtained as the precipitate, by vaporizing and removing methanol and drying the precipitate, could be reutilized as a synthesis raw material for synthesis of the compound A. The reaction liquid (60% methanol) containing the compound A obtained as a filtrate was diluted two-fold with purified water (Japanese Pharmacopoeia purified water) to make a 30% methanol solution. 136 g (228 mg per 1 mL of the starting reaction liquid) of a powder of calcium carbonate (Wako Pure Chemical Industries, Ltd.) was added gradually to the solution under stirring, whereupon there deposited a white precipitate of calcium citrate having low solubility. Although at first, the calcium carbonate dissolved accompanied by foaming (carbon dioxide gas), later gradually, calcium citrate having low solubility deposited from the solution. When the solution was allowed to stand for a whole day and night, unreacted citric acid mostly precipitated as calcium citrate to make a thick white turbid solution. The white turbid solution was centrifugally separated (room temperature, 1,500×g, 30 min) to be thereby separated into a precipitate and a supernatant solution, and the supernatant solution (containing a 30% methanol) containing the compound A was collected. Methanol was distilled away from the collected supernatant solution while being concentrated by an evaporator (Tokyo Rikakikai Co., Ltd.) to thereby make a thick viscous solution. Purified water was added to the viscous solution containing the concentrated compound A so as to have the same solution volume of 600 mL as that of the starting reaction liquid. One mol/L (2 N) of sulfuric acid was gradually added to the solution and the pH of the solution became 1.3 to 1.6, whereupon Ca ions in the solution deposited and precipitated as a calcium sulfate salt. The precipitate was removed by filtration and the filtrate was collected. The filtrate contained the compound A and was acidic with sulfuric acid. The solution (about 600 mL) was concentrated by an evaporator under heating in a water bath at 40° C. so as to have a volume of about 250 mL (to 200 mL). The solution as a mother liquid for crystallization of the compound A was cooled to room temperature, and then the glass wall surface was rubbed with a spatula or the like, whereupon a crystalline compound A deposit emerged; and the solution was allowed to stand as it was for a whole day and night, a white precipitate was obtained. The precipitate was separated from the mother solution by filtration, and collected after washing with a small amount of purified water to obtain a compound A crystal.

The above operation from the synthesis reaction liquid to the series of purification and crystallization of the crystalline compound A was repeatedly carried out to thereby obtain about 130 g (wet weight) of a crystal of the compound A from 3 L of the synthesis reaction liquid. A trace amount of the crystal (seed crystal) was laid aside, and the rest of the crystal was dissolved (in a warm bath at 40° C.) in purified water in a small amount as possible, and then the resultant solution was highly concentrated by an evaporator, and thereafter cooled; and the crystal was obtained again by adding the seed crystal to the solution. The crystal was collected by suction filtration, and dried to thereby obtain 113 g of a crystallized compound A. In order to confirm the precision of the obtained compound A crystal, the evaluation was carried out (FIG. 2) by similarly using the HPLC qualitative analysis in the confirmation of the compound A in the synthesis solution (FIG. 1). FIG. 2 shows an HPLC chromatogram of the compound A crystal which is crystallized in the aqueous solution. Specifically, the compound A purified from the synthesis reaction liquid after the heat reaction was crystallized in the aqueous solution, and the resultant crystal was purified by recrystallization, and thereafter evaluated by HPLC. 70 mg of the crystallized compound A was weighed, and dissolved in 1 mL of purified water. The resultant solution was diluted 160-fold with a mobile phase solvent (10 mM perchloric acid solution) of the HPLC analysis system, and analyzed. A clear peak of the compound A was observed, and other peaks corresponding to impurities were nearly trace intensities and not clear, it was thus confirmed that the compound A was highly purified.

Further, a noncrystal of the compound A had hygroscopicity and when being concentrated and solidified, was converted to a hygroscopic and highly viscous (glutinous) form, which was hardly handled. On the other hand, the crystal of the compound A was a non-hygroscopic powder, which was easily handled.

Example 4

(Purification of the Noncrystalline Compound A)

The solution from which the crystal of the compound A had been collected by the above-mentioned method and which became a crystal mother liquid obtained as a filtrate was used as a material for purification of the compound A not being crystallized. It was confirmed by qualitative analysis using HPLC that the compound A remained in the solution (FIG. 3). FIG. 3 shows an HPLC chromatogram of the filtrate from which after the compound A was crystallized, the crystal had been collected. The filtrate was diluted 400-fold with a mobile phase solvent (10 mM perchloric acid solution) of qualitative analysis using HPLC, and analyzed. The peak of the compound A was observed as the main peak, and peaks of other components being impurities were also observed.

About 1 L of the crystal mother solution obtained from 3 L of the synthesis reaction liquid was concentrated by using an evaporator in a water bath at 40° C. to thereby obtain about 200 mL of a concentrated liquid having a high viscosity. About 800 mL of acetone (Wako Pure Chemical Industries, Ltd.) was added and mixed with the concentrated liquid, whereupon the liquid became whitely turbid, and then after about 1 hour, white turbid components precipitated and a glutinous liquid deposit precipitated. The supernatant and the viscous deposit were separated. A crystalline deposit containing calcium citrate was obtained from the viscous deposit. The supernatant was again concentrated by using an evaporator to thereby make a concentrated solution having a high viscosity. The concentration by the solvent distilling-away and the dissolving in acetone were repeated three times to thereby replacing water-moisture in the solution by acetone (dehydration of the solution by acetone). In the process of the acetone dehydration, along with the reduction of water-moisture, a white crystalline deposit increased gradually. The resultant was finally made into 500 mL of an acetone solution, and when the solution was then allowed to stand for a whole day and night, a white crystalline deposit precipitated. The precipitate and the supernatant acetone solution were separated by filtration. It was found by a later analysis that the white deposit was the crystalline compound A (FIG. 4). FIG. 4 shows an HPLC chromatogram of compound A as a crystal purified by recrystallization, which has been crystallized in acetone. Specifically, the filtered crystal was purified by being recrystallized with purified water; the recrystallized crystal (about 20 mg) was dissolved in purified water (about 0.5 mL); and the resultant solution was diluted 40-fold with a mobile phase solvent (10 mM perchloric acid solution) of qualitative analysis using HPLC, and analyzed. A clear peak of the compound A was observed, and peaks of impurities were nearly trace intensities and not clear. By the processes hitherto, almost all of the crystalline compound A diastereomer in the crystal mother solution was crystallized, and almost all of the compound A dissolved in the acetone solution was the diastereomer of the compound A which was mostly noncrystalline.

Then, the operation in which 500 mL of purified water was added to the acetone solution containing the diastereomer of the compound A which was noncrystalline, and acetone was distilled away by an evaporator was repeated three times to thereby convert the solution solvent to water.

100 g of calcium chloride was added to the resultant aqueous solution (solution volume: about 200 mL) and calcium hydroxide was further added to make the solution pH to be 3.6. By this treatment, the compound A, an acidic substance, was derived to a calcium salt. The solution was diluted with purified water to be volume of 300 mL, and added 700 mL of ethanol to make a 70% ethanol solution, whereupon a calcium salt of the compound A deposited as a white precipitate. The precipitate was separated from the supernatant solution by centrifugal separation, and further purified by being washed with 70% ethanol to thereby obtain a purified precipitate (noncrystalline compound A Ca salt (1)). On the other hand, on examining by qualitative analysis using HPLC, the supernatant solution made to be a 70% ethanol solution included remaining compound A, and the solution was adjusted the pH to 6.0 as a condition for more strongly inducing the Ca salt from compound A, and then by making the solution to be a 80% ethanol solution, a precipitate was obtained. The precipitate was washed with ethanol to make a purified precipitate (noncrystalline compound A Ca salt (2)).

The purified precipitate obtained at a pH of 3.6 by the above operation and the purified precipitate obtained at a pH of 6.0 thereby were each evaluated by qualitative analysis using HPLC (FIG. 5, FIG. 6). The each precipitate (about 10 mg) was dissolved in purified water (about 1 mL), diluted 40-fold with a 10 mM perchloric acid solution being a mobile phase of the qualitative analysis using HPLC, and analyzed (by being diluted with the 10 mM perchloric acid solution, which was an acidic solvent, the Ca salts of the compound A were converted to the compound A, thus the detection was made as the compound A.). FIG. 5 is an HPLC chromatogram of the precipitate deposited at a pH of 3.6; and FIG. 6 is an HPLC chromatogram of the precipitate deposited at a pH of 6.0. In the HPLC chromatogram of the purified precipitate (noncrystalline compound A Ca salt (1)) obtained at a pH of 3.6, although peaks of impurities are observed, the main peak of the compound A is strongly observed, revealing that the precipitate was purified. On the other hand, in the HPLC chromatogram of the purified precipitate (noncrystalline compound A Ca salt (2)) obtained at a pH of 6.0, together with the peak of the compound A (peak 2), there is observed mingling of a compound (a peak overlapping on the left shoulder of the peak of the compound A) amidated by hydrolysis of a part of the imide structure of the compound A, and a peak (peak 3) supposed to be citric acid becomes increased. Therefore, it was conceivable that the hydrolysis of the compound A progressed by the amount of the alkali, which added for the pH to be 6.0, and that the condition as depositing the Ca salt of the compound A was too severe. Since the Ca salt of the compound A deposited at a pH of 3.6 had only a tiny amount mingled of the hydrolyzate of the compound A, it was conceivable that the pH of 3.6 was the limit of the alkali condition.

By dissolving the precipitate of the Ca salt of the compound A deposited in the ethanol solution, in water, and by making the resultant solution to be acidic with sulfuric acid (for example, a pH of 1.3) to thereby deposit calcium sulfate, calcium content could be removed and the compound A as a sulfuric acid acidic solution could be prepared. By this purifying process, there was obtained 192.7 g of a dry solid of the noncrystalline compound A Ca salt (1) being a purified precipitate obtained at a pH of 3.6 from 3 L of the synthesis reaction liquid.

Example 5

(Qualitative Analysis Using HPLC of the Compound A Diastereomers)

The presence ratio of the compound A diastereomers as the purified substances obtained in the purifying process from the above compound A synthesis solution was confirmed by qualitative analysis using HPLC using the following column. Solutions having various concentrations of the compound A were diluted with a mixed liquid (mobile phase for qualitative analysis using HPLC) of a 0.1% TFA aqueous solution (98 in volume) and methanol (2 in volume); and undissolved substances were removed by a membrane filter; and the solution was analyzed by high performance liquid chromatography. The conditions of the qualitative analysis using HPLC were as follows. The objective component supposed to be the compound A in the chromatogram was detected as two adjacent peaks in the range of a retention time (RT) of 3.3 to 3.7 min (however, RT slightly changed in some cases, due to the influence such as deterioration of the column packing material). The crystalline compound A diastereomer was detected as a peak on the right side of the longer retention time in the column; and the noncrystalline compound A diastereomer was detected as a peak on the left side of the shorter retention time.

(Separation Condition in the Qualitative Analysis Using HPLC)

Apparatus: Shimadzu Corp., High Performance Liquid Chromatograph Prominence
Column: Phenomenex Kinetex F5 (100 mm×4.6 mm)
Mobile phase: a mixed liquid of a 0.1% TFA aqueous solution (98 in volume) and methanol (2 in volume)
Flow rate: 0.8 mL/min
Column temperature: 30° C.
Injection volume: 5 µL
Detection wavelength: 200 nm Example 6

(Results of Analysis of Diastereomers in Samples Containing the Compound A)

By the HPLC qualitative analysis using the column mentioned above, the presence state of diastereomers in purified samples from the compound A synthesis solution was confirmed.

(1) Compound A Synthesis Solution

There was confirmed the presence state of the compound A diastereomers in a roughly purified compound A synthesis solution made by removing most part of unreacted aspartic acid and citric acid from the compound A synthesis solution (FIG. 7). FIG. 7 shows an HPLC chromatogram of the roughly purified compound A synthesis solution. Tow diastereomers of the compound A were detected as two adjacent peaks, and their presence ratio was nearly equal.

(2) Compound A Crystal

The compound A crystal obtained by being purified from the compound A synthesis solution and being crystallized in the aqueous solution was dissolved in purified water and the presence state of the compound A diastereomers was evaluated by qualitative analysis using HPLC (FIG. 8). FIG. 8 shows an HPLC chromatogram (analysis result for the same sample as in FIG. 2) of the compound A crystallized in the aqueous solution. The crystalline compound A was detected as a peak on the right side of a longer retention time in the range of detection of two compound A diastereomers, and its presence ratio was 99% or higher in peak areal ratio. The mingling ratio of the other diastereomer was 0.36% (calculated from the peak areal ratio).

(3) Compound A Crystal Crystallized in Acetone

The compound A crystal obtained by being purified from the compound A synthesis solution and being crystallized in acetone was dissolved in purified water and the presence state of the compound A diastereomers was evaluated by qualitative analysis using HPLC (FIG. 9). FIG. 9 shows an HPLC chromatogram (analysis result for the same sample as in FIG. 4) of the compound A crystallized in acetone. The crystalline compound A crystallized in acetone, similarly to the crystalline compound A crystallized in the aqueous solution, was detected as a peak on the right side of a longer retention time in the range of detection of two compound A diastereomers, and its presence ratio was 98% or higher in peak areal ratio. The mingling ratio of the other diastereomer was 1.36% (calculated from the peak areal ratio).

(4) Ca Salt of the Noncrystalline Compound A (1) Precipitated at a pH of 3.6 in a 70% Ethanol (Noncrystalline Compound A Ca Salt (1))

After the compound A to be crystallized in the compound A synthesis solution was crystallized, the noncrystal compound A remaining in the solution was converted to a Ca salt by the condition of a pH of 3.6, and deposited as a precipitate in a 70% ethanol; and the presence state of diastereomers of the compound A of the precipitate was evaluated by qualitative analysis using HPLC (FIG. 10)(the same deposit sample as the sample of FIG. 5). FIG. 10 shows an HPLC chromatogram (analysis result for the same sample in FIG. 5) of the noncrystalline compound A Ca salt (1) deposited at a pH of 3.6 (noncrystalline compound A Ca salt (1)). The precipitate deposited in the 70% ethanol was dissolved in purified water, subjected to qualitative analysis using HPLC and was detected as a peak on the left side of the shorter retention time in the range of detection of two compound A diastereomers. The peak was detected as a peak on RT clearly different from the peak of the crystalline compound A. Its presence ratio was 99% or higher in peak areal ratio. The mingling ratio of the other diastereomer (crystalline compound A) was 0.45% (calculated from the peak areal ratio).

(Interpretation: since peaks in each chromatogram are tailing backward (a phenomenon of the feet of the peaks extending), the peak areal ratios are smaller than the visual peak heights of the mingling peaks.)

Example 7

(Manufacture of the Crystal of the Compound A by Ion Exchange Chromatography)

1. Purification of the Starting Substance 1-1. Preparation of the Starting Substance Water was added to 75 g (0.59 mol) of citric acid (monohydrate) to thereby prepare 83.3 mL of a thick citric acid solution; 10 g (0.111 mol) of L-asparagine and 1.5 g (0.019 mol) of L-aspartic acid were added to the solution; and the resultant solution was diluted to a solution volume of 100 mL. The reaction liquid was put in a pressure-resistant glass vessel and sealed therein, and heated in a water bath at 90° C. to thereby completely dissolve the L-asparagine and L-aspartic acid added. Then, the reaction liquid in the pressure-resistant vessel was put in an autoclave heated at about 80° C., and heat treated at 121° C. for 180 min. After the reaction, the reaction liquid was spontaneously cooled to 25° C., and thereafter was taken out to a 1-L beaker, and ice cooled.

About 20 g of sodium hydroxide was dissolved in 83 mL of purified water; this sodium hydroxide aqueous solution was ice cooled, and gradually added to the above reaction liquid to neutralize the reaction liquid to a pH of 5.8 (since the heat generation occurred due to the heat of neutralization, the neutralization was carried out while checking that the temperature is 25° C.). After the neutralization, the volume of the reaction liquid was made to be 200 mL by purified water. Then, 33.3 g of calcium chloride (dihydrate) was dissolved in 0.33 L of purified water to prepare a calcium chloride solution; about a half volume thereof was added to the above reaction liquid, well stirred and allowed to stand for about 16 hours. In the solution, a white precipitate (calcium citrate) deposited. Since when the calcium chloride solution was further added, a white precipitate was newly precipitated, the calcium chloride solution was gradually added and about 333 mL (0.23 mol as the amount of calcium chloride) was resultantly added to 200 mL of the neutralized reaction liquid. Purified water was added to the resultant mixed solution so that the total volume became 600 mL, and thereafter, a white precipitate being calcium citrate was removed by centrifugal separation and the supernatant was recovered. Then, 430 mL of the supernatant was concentrated to 133 mL by an evaporator (since heat was intended not be applied, the bath temperature was made to be 25° C.). 310 mL of ethanol was added to the concentrated aqueous solution and stirred. When the resultant mixed liquid was allowed to stand for a while, the mixed liquid was separated into two layers, which were a relatively transparent upper layer (ethanol layer) and 50 mL of a lower layer solution having coloration and viscosity. The lower layer was separated and recovered, and diluted with purified water to about 130 mL; and thereafter, ethanol remaining in the solution was distilled away by an evaporator (since heat was intended not be applied, the bath temperature was made to be 25° C.) to thereby make 55 mL of the solution. The solution was centrifugally separated to thereby obtain 45 mL of a supernatant. The supernatant was lyophilized to thereby obtain 32.67 g of the resultant. The resultant was used as a starting substance.

1-2. Ion Exchange Column Chromatography (SuperQ)

280 mL (aqueous solution, solid content: 235 g) of the starting substance prepared by the above method was dissolved in 1 L of purified water; about 13 mL of a 25% aqueous ammonia and 19 L of purified water were added in order to adjust pH and the electroconductivity to thereby make a sample to be introduced (pH: 7.1, electroconductivity: 8.4 mS/cm). This was fed to ion exchange column chromatography (TOYOPEARL SuperQ-650M, φ150 mm×500 mm). The details of the mobile phase and each separated fraction are shown in FIG. 11. The two target substance fractions were each lyophilized to thereby obtain substances indicated in Table 1 in FIG. 11. The estimated content of the target substance in two target substance fractions (Fr (fraction) 8 to 12 and Fr13 was calculated as 5.4 g, and the recovery rate to 64.1 g of the estimated content of the target substance in the raw material was 86.4%. Here, Lot. Nos. in the Table 1 are numbers attached to the two target substance fractions for convenience.

1-3. Removal of Ammonium Acetate by Ion Exchange Column Chromatography (DOWEX 50Wx8), and Lyophilization 740.2 g of Fr8 to 12 (Lot. No. 198-012-74-1) was dissolved in about 600 mL of purified water, and subjected to the batchwise treatment with an ion-exchange resin (DOWEX 50Wx8, H+ type, 100 to 200 mesh), and thereafter was lyophilized. The lyophilized product was again dissolved in 800 mL of purified water, and divided into two parts and introduced to ion exchange column chromatography (DOWEX 50Wx8, H+ type, 150 mm×200 mm). After the introduction, purified water was fed, and fractions containing the target substance were collected and lyophilized. The operation in which purified water was added to the dried residue, and the resultant was lyophilized was repeated several times to thereby reduce acetic acid. At this time, since crystallization occurred in purified water, a crystal and a mother liquid were separated by suction filtration. The resultants were each lyophilized to thereby obtain the following.

The crystal of the compound A: 16.5 g (Lot. No. 198-012-078-1, white crystal, see an HPLC chromatogram of FIG. 12, see a 1H NMR spectrum of FIG. 13)

The mother liquid (containing the compound A) after the crystal of the compound A had been fractionally collected: 36.1 g (Lot. No. 198-012-078-2, milk white amorphous state, see an HPLC chromatogram of FIG. 14, see a 1H NMR spectrum of FIG. 15).

2. Summary

The following could be obtained from 280 mL (aqueous solution, solid content: 235 g) of the starting substance by the ion exchange column chromatography. There is shown in Table 1, the estimated content of the target substance (compound A) calculated from the acetic acid content calculated by $^1$H NMR and the area value of HPLC. The total target substance content of the three Lots obtained this time's purifying process was calculated as 54.2 g and the recovery rate from the starting substance (estimated content of the target substance: 64.1 g) was 84.5%.

As described above, it was shown that by the purification by ion exchange column chromatography, the crystal could be crystallized from the aqueous solution of the compound A.

present invention obtained in the above Examples were crystalline or noncrystalline (amorphous) is confirmed.

2. Samples

There were used as samples, the crystal of the compound A obtained from the aqueous solution by column purification in Example 7 (test sample 1), the crystal of the compound A obtained from the acetone solution in Example 4 (crystal stored as seed crystal and not recrystallize)(test sample 2), and the Ca salt (1) of the noncrystalline compound A (the noncrystalline diastereomer of the compound A) obtained in the manufacturing method in Example 4 (test sample 3).

3. Analysis Method 3.1. Apparatus
RINT-TTRIII type wide-angle X-ray diffractometer, manufactured by Rigaku Corp.
X-ray source: CuKα radiation
Tube voltage-tube current: 50 kV-300 mA
Step width: 0.02 deg.
Measurement speed: 5 deg./min
Slit system: divergence-reception-scattering
   0.5 deg.-0.15 mm-0.5 deg.
Diffraction line curved crystal monochrometer
3.2. Method
Powders of the test sample 1 to the test sample 3 were measured as they were.

4. Results

FIG. 16 shows comparison by multiple plotting of powder X-ray diffractometric patterns of respective substances of the test sample 1 (the crystal obtained from an aqueous solution by column purification), the test sample 2 (the crystal obtained from an acetone solution) and the test sample 3 (the Ca salt of the noncrystalline diastereomer).

TABLE 1

| Item Name | Lot. No. | Weight (g) | Yield (%)*1 | HPLC Purity (%)*4 | Estimated Content Percentage of Acetic Acid (w/w %)*2 | Estimated Content of Target Substance (g)*3 |
|---|---|---|---|---|---|---|
| Crystal of Compound A | 198-012-078-1 | 16.5 | 7.0 | 99.5 | — | 16.5 |
| Mother Liquid after Fractional Collection of Crystal of Compound A | 198-012-078-2 | 36.1 | 15.4 | 91.9 | 1 | 29.3 |
| (Reference) Starting Substance | — | 235 | — | 75.4 | — | 64.1 |

*1 The yield was calculated provided the solid content of the starting substance was 235 g.
*2 The acetic acid content was calculated from $^1$H NMR.
*3 The estimated content of the target substance was calculated from a one-point calibration curve of an HPLC areal value with the peak of the crystal of the compound A obtained this time being used as a reference.
*4 The "HPLC purity" represented a purity as the compound A.

Example 8

(Powder X-Ray Diffractometry)
The measurement of powder X-ray diffraction was carried out by using the crystal of the compound A and the noncrystalline diastereomer of the compound A according to the present invention by the following method.
1. Purpose
Whether the crystal of the compound A and the noncrystalline diastereomer of the compound A according to the Further, the peak list of the powder X-ray diffraction of the test sample 1 is shown in Table 2; and that of the test sample 2, in Table 3.

As is clear from FIG. 16 (in the upper pattern and in the middle pattern) and Table 2 and Table 3, in the test sample 1 and the test sample 2 each, clear peaks were observed in the diffraction pattern by the powder X-ray diffractometry, and it was confirmed that they were crystalline solids. Further since the diffraction patterns by the powder X-ray diffractometry of the test sample 1 and the test sample 2 coincided with each other, it was also confirmed that the both were crystals having the same shape.

On the other hand, as is clear from FIG. 16 (in the lower pattern), in the test sample 3 being a solid obtained by adding ethanol to solidify the noncrystalline diastereomer as the Ca salt, no clear peak was observed in the powder X-ray diffraction pattern, and it was confirmed that it was an amorphous (noncrystalline) solid.

TABLE 2

| Diffraction Angle (2θ) | Relative Intensity (%) |
| --- | --- |
| 11.735 | 96.8 |
| 12.938 | 27.4 |
| 15.719 | 19.8 |
| 15.901 | 71.9 |
| 16.180 | 54.7 |
| 16.678 | 42.3 |
| 17.838 | 36.4 |
| 18.119 | 30.7 |
| 18.359 | 88.4 |
| 19.042 | 62.9 |
| 19.301 | 75.5 |
| 21.181 | 37.0 |
| 21.759 | 87.7 |
| 23.561 | 21.5 |
| 24.101 | 85.0 |
| 26.400 | 43.5 |
| 26.959 | 70.3 |
| 28.698 | 33.7 |
| 29.261 | 100 |
| 36.240 | 19.1 |

The top 20 relative intensities were extracted.

TABLE 3

| Diffraction Angle (2θ) | Relative Intensity (%) |
| --- | --- |
| 11.741 | 100 |
| 12.938 | 22.4 |
| 15.959 | 81.3 |
| 16.196 | 40.4 |
| 16.682 | 35.7 |
| 17.859 | 37.2 |
| 18.158 | 31.6 |
| 18.359 | 66.7 |
| 19.038 | 55.6 |
| 19.200 | 35.3 |
| 19.337 | 65.0 |
| 21.198 | 32.8 |
| 21.742 | 70.1 |
| 23.582 | 23.0 |
| 24.081 | 65.1 |
| 26.441 | 39.3 |
| 26.941 | 54.5 |
| 29.238 | 87.0 |
| 29.644 | 28.9 |
| 36.258 | 20.2 |

The top 20 relative intensities were extracted.

Example 9

(Determination of the Configuration of the Crystalline Compound A)

A single crystal of the compound A for structural analysis by single crystal X-ray diffractometry was produced by the following method and was subjected to structural analysis by single crystal X-ray diffractometry.

1. Purpose

When the compound A was synthesized by the method as noted above, citric acid was bonded to a structure derived from L-aspartic acid (S isomer) by an imidization reaction and there was synthesized two diastereomers (SS isomer and SR isomer) shown in the below. One out thereof had a property of being crystallized and the other had a property of not being crystallized. Although the two diastereomers each can be separated and purified due to this difference, there cannot be specified so far which one is an SS isomer or an SR isomer. In order to solve this problem, there was produced a single crystal having a size of 0.2 mm cube or larger of the crystalline compound A, and was subjected to the structural analysis by single crystal X-ray diffractometry.

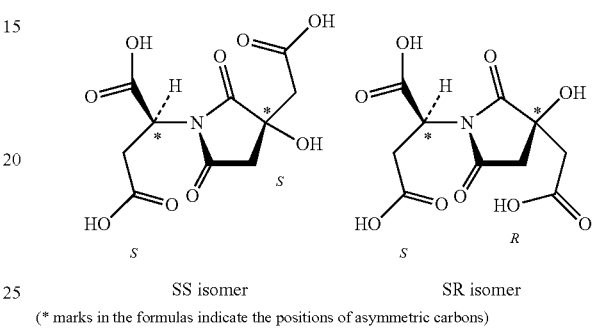

SS isomer      SR isomer (* marks in the formulas indicate the positions of asymmetric carbons)

Even if the compound A was crystallized in a solvent such as water or acetone by the method as noted above, there could not be obtained a single crystal in such a size that is able to carry out the structural analysis by the single crystal X-ray diffractometry. Therefore, the solvent system and the crystallization method in order to obtain a single crystal of the compound A were studied, and the method was established to produce a single crystal in a size level usable for the structural analysis by the single crystal X-ray diffractometry, then the analysis was carried out.

2. Study of the Condition of the Production of the Single Crystal of the Compound A By using, as a raw material, the compound A obtained by further purifying the crystal of the compound A synthesized, purified and crystallized in the aqueous solution by the method as noted above, by recrystallization as noted above in Example 3, the production of the single crystal for the structural analysis by the single crystal X-ray diffraction has been investigated.

A highly purified crystalline powder of the compound A was obtained by repeating three times the same operation as in the recrystallization as noted above in Example 3. 100 mL of purified water (Japanese Pharmacopoeia purified water) was added to 10 g of the crystalline powder, which was then dissolved by heating the resultant in a water bath at 50° C. The resultant solution was filtered by using a membrane filter (Merck Millipore) of 0.22 μm in pore size, and the resultant filtrate was collected. The filtrate was concentrated by using an evaporator on a water bath at 40° C. to thereby collect the resultant as an about 50 ml of a solution. This solution was concentrated and cooled to room temperature to thereby become a solution in a supersaturated state. The solution as it was in the heated state (40° C.) was dispensed in test tubes with a lid so as to have solvent ratios indicated in the following Table (Table 4) to thereby produce solutions having mixed solvents. Specifically, by adding 100 μL of organic solvents of methanol, ethanol, acetone and the like to 400 μL of the supersaturated solution, there was made a solution having a water ratio in the mixed solvent of 80%.

Similarly, by adding 200 μL, 300 μL and 400 μL of the organic solvents of methanol, ethanol, acetone and the like to 300 μL (water: 60%), 200 μL (water: 40%) and 100 μL (water: 20%) of the supersaturated solution, respectively, there were produced solutions having mixed solvents having water ratios in the mixed solvents of 60%, 40% and 20%, respectively. With regard to the solution having 100% of water, 500 μL of the supersaturated solution as it was dispensed. With regard to the solution having 100% of the organic solvents of methanol, ethanol, acetone and the like, 50 mg of the highly purified crystal of the compound A was put in a test tube; 500 μL of the solvent was added; and as much of the crystal as possible was dissolved by being heated at 40° C. In mixed solvent systems of isopropanol and water, when the ratio of isopropanol was 40% or higher, since the solubility of the compound A decreased and much of a precipitate quickly deposited, there was carried out no study on 40% or higher of isopropanol in the mixed solvent systems. The results are shown in Table 4.

TABLE 4

| Proportion of Water | 100% | 80% | 60% | 40% | 20% | 0% |
|---|---|---|---|---|---|---|
| Water | 100% | | | | | |
| Methanol | | 20% | 40% | 60% | 80% | 100% |
| Ethanol | | 20% | 40% | 60% | 80% | 100% |
| Isopropanol | | 20% | 40% | — | — | — |
| Acetone | | 20% | 40% | 60% | 80% | 100% |

The test tube of the each solution of the compound A thus produced was hermetically closed—with the lid of the test tube, and allowed to stand at room temperature for a whole day and night or longer to thereby make the compound A to deposit from the supersaturated state. Each of the test tube was subjected to centrifugal separation (room temperature, 3,000 rpm, 10 min) to thereby make deposits to precipitate down; and a supernatant of the each solution was cautiously transferred to another clean test tube with a plastic lid to thereby make a saturated solution of the each solution. In the state that the lid of the test tube of the each saturated solution was closed, a pinhole was opened on the plastic lid by an injection needle, and the test tube was allowed to stand at room temperature while the solvent slowly evaporated through the pinhole and so the crystal of the compound A thereby deposited. By observing the shape and the size of the deposited crystal and the situation of the crystal growth with time, it has been found that suitable was a method of crystallization of the crystal by using the mixed solution system of water and acetone. With regard to the solvent ratio, an acetone ratio of 40% to 80% (a water ratio of 60% to 20%) was good, and best was the crystal obtained by evaporating a saturated solution particularly having an acetone ratio of 60% (water ratio of 40%). In alcohol-based solvent systems other than the acetone system, polycrystallization was liable to occur, or the crystal growth was poor, so there was obtained no single crystal usable for the single crystal X-ray diffractometry.

3. Production of the Single Crystal of the Compound A

For the structural analysis of the compound A by single crystal X-ray diffractometry, there was used crystals obtained by slowly evaporating the water-acetone (40%-60%) mixed solvent at room temperature through by opening a pinhole on the lid of the test tube in which the saturated solution of the mixed solvent was put. The crystals were made to grow over several days until crystallized single crystals sufficiently grew, and collected before the single crystals fused and polycrystallized. The collecting procedure of the crystals involved turning the test tube upside down together with the solution containing the crystals to drop the solution on a filter paper to thereby make the solution to be absorbed in the filter paper and collecting the crystals left on the filter paper by a metal needle. The collected single crystals were observed under a mesoscope, and there were picked out single crystals having sizes and shapes usable for the structural analysis by single crystal X-ray diffractometry, and used for the structural analysis by single crystal X-ray diffractometry.

4. Structural Analysis of the Compound A by Single Crystal X-Ray Diffractometry

Structural analysis by single crystal X-ray diffractometry was carried out in order to examine which one of an SS isomer and an SR isomer the crystallized compound A was. A prismatic crystal (0.2 mm×0.2 mm×0.6 mm) having good crystallinity was sampled out of the single crystals produced according to the above method for producing single crystals, thereafter mounted on a glass fiber, and subjected to X-ray diffractometry using a RASA-7R type of tetra-axial diffractomter, manufactured by Rigaku Corp., using a CuKα radiation ($\lambda$=1.54178 Å) monochromatized by a graphite monochrometer.

The lattice constant was determined by the method of least squares from 25 reflections in the range of $50.0° < 2\theta < 58.8°$. The measurement was carried out on reflections of diffraction angles $2\theta$ of 136.1° or lower by the ω-2θ scanning method. After the measurement of all reflection data, it was found by the extinction rule (systematic reflection intensity extinction) that the space group was $P2_{1/c}$(#14). The measurement data are shown in Table 5, and the crystal data are shown in Table 6.

[Table 5]<Measurement Data>
Diffractometer used: RASA-7R type, manufactured by Rigaku Corp.
Scanning method: ω-2θ
Scanning width: 1.79°+0.30° tan θ
Scanning speed (ω): 16.0°/min
Data collection range: 2θmax 136.1°
Number of reflections: 2,552
Number of independent reflections: 1,902
Criterion adopted as observation values: I>3σ(I)
Number of reflections adopted as observation values: 1,899
Correction: Lorentz factor and polarization factor
Extinction effect correction coefficient: 4.24060e+001

[Table 6]<Crystal Data>
Molecular formula: $C_{10}H_{11}NO_9+H_2O$
Molecular weight: 289+18
Crystal system: monoclinic
Space group: $P2_{1/c}$(#14)
a: 11.685(2) Å
b: 10.262(3) Å
c: 11.129(2) Å
α: 90°
β: 107.46(1)°
γ: 90°
Volume of unit cell: 1,273.2(4) Å$^3$
X-ray used and wavelength thereof: CuKα radiation ($\lambda$=1.54178 Å)
Number of molecules in unit cell: Z4
Calculated value of density: 1.603 g/cm$^3$
Linear absorption coefficient (CuKα): 12.99 m$^{-1}$
Shape and size of sample crystal: prism shape (0.20 mm×0.20 mm×0.60 mm)
F(000): 640.00
Measurement temperature: 25° C.

5. Determination of the Crystal Structure of the Compound A

The structural determination was carried out by using the direct method SIR92 using 280 reflections whose absolute values of standardized structural factors E were higher than 1.527. All atomic coordinates could be determined from Emap calculated from a set of phases giving the highest Figure of merit (FOM=1.416) and the structural extension by Fourier. The refinement was carried out by using 1,899 reflections whose reflection intensities I were higher than 3σ(I) and the full-matrix method of least squares. The R-factor calculated by equalizing weight rates of all the reflections converged to 0.053. The maximum value and the minimum value of the electron density in a final D Fourier diagram were 0.28 and $-0.25\text{e-}/\text{Å}^3$. The atom scattering factor used was a value described in "International Tables for X-ray Crystallography", and all calculations were carried out by using CrystalStructure being a crystallographic software package of Rigaku Corporation and Rigaku/MSC. The analysis data are shown in Table 7.

[Table 7]<Analysis Data>
Determination method of approximate structure: direct method (SIR92)
Method of least squares used: full matrix method
Kind of temperature factor: anisotropic temperature factor
Treatment of hydrogen atom: isotropic temperature factor
Final R indices: R=0.053, wR=0.043 (weight rate: $1/\sigma^2$ (Fo))
Final D Maximum value of synthetic electron density: $0.28\text{e-}/\text{Å}^3$
Final D Minimum value of synthetic electron density: $-0.25\text{e-}/\text{Å}^3$
Name of program system used: CrystalStructure As a result of the analysis, it has been clarified that the crystalline compound A (the crystal of the compound A) was enantiomers of an SS isomer and an RR isomer in the RS notation system. Then since aspartic acid used in the synthesis was all L-aspartic acid (an S isomer), it has been found that the crystalline compound A was an SS isomer. Then in response thereto, it has also been found that the compound A having a property of not being crystallized was an SR isomer.

INDUSTRIAL APPLICABILITY

Although the diastereomer mixture of the compound A is known to be an active substance having an inhibitory effect against liver disorder, there has been unknown so far the physiological action of the crystalline compound A and the noncrystalline compound A in organisms. In order to separate organic compounds having analogous structures, such as diastereomers, not limited to the compound A, there are required processes requiring a highly purifying technology generally using columns having high resolution ability. Further in usual purification means using these columns, enlargement of the purification scale is difficult and the supply thereof in a large amount requires high costs in many cases. In the present application, there has been confirmed the fact that only one diastereomer of the compound A can be crystallized and there has been established the method for purifying the diastereomer inexpensively and in a large amount according to the crystallization technology. There has also been established means of purifying the noncrystalline diastereomer inexpensively and in a large amount by almost completely crystallizing the crystalline diastereomer by using an organic solvent. Thereby, it is expected that the scale of supplying the purified diastereomers of the compound A can be expanded from the analysis level to the industrial level. Due to that according to the present invention, there are provided inexpensively and in large amounts, the crystal of the compound A and the remarkably high-purity noncrystalline diastereomer of the compound A, the compound A is expected to be efficiently applied to the field of medicine manufacture, the fields of manufacture of foods including functional foods and health foods, and the like.

The invention claimed is:

1. A crystal of a compound represented by the following formula (A) (hereinafter, referred to as compound A):

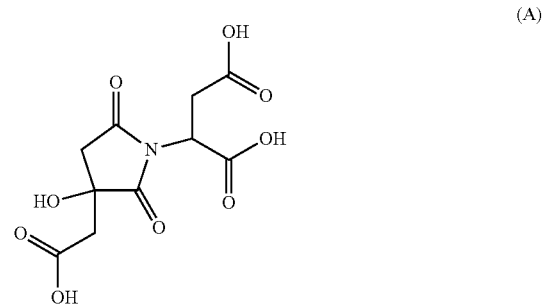 [SMILES: O=C(O)CC(C(=O)O)N1C(=O)CC(O)(CC(=O)O)C1=O]

(A)

the crystal having peaks of diffraction angles (2θ) at 11.74±0.20°, 29.25±0.20°, 18.36±0.20°, 21.75±0.20° and 15.95±0.20° in a powder X-ray diffractometric pattern using a CuKα radiation as an X-ray source.

2. The crystal according to claim 1, having a steric structure of an SS isomer in the RS notation system.

3. A method for manufacturing the crystal according to claim 1, comprising the following (a) to (f):
   (a) passing an aqueous solution containing the compound A and/or a salt thereof and citric acid and/or a salt thereof and having a pH of 5.0 to 8.5 through a column packed with an anion-exchange resin;
   (b) passing an eluent through the column to thereby acquire an aqueous solution containing no citric acid but containing the compound A;
   (c) removing the eluent from the aqueous solution obtained by (b);
   (d) concentrating the aqueous solution from which the eluent has been removed;
   (e) adding water to the concentrated residue to make an aqueous solution, and concentrating the aqueous solution to thereby deposit a crystal of the compound A; and
   (f) acquiring the crystal of the compound A.

4. The manufacturing method according to claim 3, wherein the eluent is an eluent selected from the group consisting of an ammonium acetate aqueous solution, a sodium chloride aqueous solution and an ammonium formate aqueous solution.

5. The manufacturing method according to claim 3, wherein a method of removing the eluent is a method using a column packed with a cation-exchange resin.

6. The manufacturing method according to claim 3, wherein a method of the concentration is lyophilization.

7. A method for manufacturing the crystal according to claim 1, comprising the following (a) to (f):
   (a) adding calcium carbonate to an aqueous solution containing the compound A and citric acid and having a pH of 2.0 or lower to thereby deposit calcium citrate;
   (b) removing calcium citrate from the aqueous solution;
   (c) adding sulfuric acid to the aqueous solution to make the pH to be 2.0 or lower to thereby deposit calcium sulfate;

(d) removing calcium sulfate from the aqueous solution;
(e) concentrating the aqueous solution to thereby deposit a crystal of the compound A; and
(f) acquiring the crystal of the compound A.

8. The manufacturing method according to claim 7, wherein the concentration is vacuum concentration.

9. The manufacturing method according to claim 7, further comprising, after acquiring the crystal of the compound A, the following (g) to (j):
   (g) adding an organic solvent to the aqueous solution to thereby deposit calcium citrate;
   (h) removing calcium citrate from the mixed liquid of the aqueous solution and the organic solvent;
   (i) dehydrating the mixed liquid of the aqueous solution and the organic solvent to thereby deposit a crystal of the compound A; and
   (j) acquiring the crystal of the compound A.

10. The manufacturing method according to claim 9, wherein the organic solvent is acetone.

\* \* \* \* \*